(12) United States Patent
Fryshman

(10) Patent No.: US 11,055,579 B2
(45) Date of Patent: *Jul. 6, 2021

(54) INDUCTION HEATING SYSTEMS

(71) Applicant: Bernard Fryshman, Brooklyn, NY (US)

(72) Inventor: Bernard Fryshman, Brooklyn, NY (US)

(73) Assignee: Bernard Fryshman, Brooklyn, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/930,384

(22) Filed: Jul. 16, 2020

(65) Prior Publication Data

US 2020/0349398 A1    Nov. 5, 2020

Related U.S. Application Data

(63) Continuation of application No. 16/891,267, filed on Jun. 3, 2020, which is a continuation-in-part of (Continued)

(51) Int. Cl.
*H05B 6/10* (2006.01)
*G06K 9/62* (2006.01)
(Continued)

(52) U.S. Cl.
CPC ........... *G06K 9/6267* (2013.01); *A01H 1/027* (2021.01); *A01M 1/026* (2013.01); *A01M 1/06* (2013.01); *A01M 1/14* (2013.01); *A01M 1/20* (2013.01); *A01M 1/2094* (2013.01); *A01M 1/22* (2013.01); *A01M 1/226* (2013.01); *A01M 3/005* (2013.01); *A01M 3/007* (2013.01); *A01M 5/02* (2013.01); *A01M 5/04* (2013.01); *A01M 7/00* (2013.01); *A01M 99/00* (2013.01); *B64C 39/024* (2013.01); *B64D 1/18* (2013.01); *B64D 47/08* (2013.01); *G06K 9/00* (2013.01); *G06K 9/6256* (2013.01); *G06T 3/40* (2013.01); *G06T 7/0004* (2013.01);
(Continued)

(58) Field of Classification Search
None
See application file for complete search history.

(56) References Cited

U.S. PATENT DOCUMENTS 8,275,413 B1 * 9/2012 Fraden ............... G01J 1/429
455/556.1
8,845,961 B2 * 9/2014 Bernstein ............ C09K 11/663
422/23

(Continued)

*Primary Examiner* — Anand P Bhatnagar
(74) *Attorney, Agent, or Firm* — Bell & Manning, LLC; Christopher Kalafut

(57) ABSTRACT

A method for performing mold remediation includes placing a ferromagnetic material in or adjacent to a surface upon which mold is located. The method also includes emitting, by an electromagnetic radiation source, radiation to heat the ferromagnetic material that is adjacent to the surface upon which the mold is located. The method also includes detecting, by a temperature sensor, a temperature of the surface. The method further includes comparing, by a processor in communication with the electromagnetic radiation source and the temperature sensor, the temperature of the surface to a desired temperature to perform mold remediation.

20 Claims, 18 Drawing Sheets

Related U.S. Application Data application No. 16/575,907, filed on Sep. 19, 2019, now Pat. No. 10,694,588, which is a continuation-in-part of application No. 16/393,445, filed on Apr. 24, 2019, now Pat. No. 10,425,996, which is a continuation-in-part of application No. 16/238,602, filed on Jan. 3, 2019, now Pat. No. 10,339,426, which is a continuation-in-part of application No. 16/100,489, filed on Aug. 10, 2018, now Pat. No. 10,185,896, which is a continuation-in-part of application No. 16/035,919, filed on Jul. 16, 2018, now Pat. No. 10,229,348, which is a continuation-in-part of application No. 15/956,083, filed on Apr. 18, 2018, now Pat. No. 10,043,263, which is a continuation-in-part of application No. 15/919,541, filed on Mar. 13, 2018, now Pat. No. 10,026,165, which is a continuation-in-part of application No. 15/802,814, filed on Nov. 3, 2017, now Pat. No. 9,965,850, which is a continuation-in-part of application No. 15/654,390, filed on Jul. 19, 2017, now Pat. No. 9,852,362, which is a continuation-in-part of application No. 15/425,079, filed on Feb. 6, 2017, now Pat. No. 9,811,764, which is a continuation of application No. 15/153,621, filed on May 12, 2016, now Pat. No. 9,563,945, which is a continuation-in-part of application No. 14/733,044, filed on Jun. 8, 2015, now Pat. No. 9,381,646, which is a continuation-in-part of application No. 14/505,430, filed on Oct. 2, 2014, now Pat. No. 9,053,528, which is a continuation-in-part of application No. 13/542,416, filed on Jul. 5, 2012, now Pat. No. 8,855,374.

(60) Provisional application No. 62/551,345, filed on Aug. 29, 2017, provisional application No. 62/183,591, filed on Jun. 23, 2015, provisional application No. 61/504,462, filed on Jul. 5, 2011.

(51) Int. Cl.

| | | |
|---|---|---|
| *H04N 5/225* | (2006.01) | |
| *H04N 7/18* | (2006.01) | |
| *B64C 39/02* | (2006.01) | |
| *B64D 1/18* | (2006.01) | |
| *A01M 7/00* | (2006.01) | |
| *A01M 5/04* | (2006.01) | |
| *A01M 1/02* | (2006.01) | |
| *A01M 1/06* | (2006.01) | |
| *A01M 1/14* | (2006.01) | |
| *A01M 1/20* | (2006.01) | |
| *A01M 1/22* | (2006.01) | |
| *A01M 3/00* | (2006.01) | |
| *G06K 9/00* | (2006.01) | |
| *A01M 99/00* | (2006.01) | |
| *A01M 5/02* | (2006.01) | |
| *G06T 7/00* | (2017.01) | |
| *G06T 7/62* | (2017.01) | |
| *G06T 7/90* | (2017.01) | |
| *B64D 47/08* | (2006.01) | |
| *G06T 3/40* | (2006.01) | |
| *A01H 1/02* | (2006.01) | |

(52) U.S. Cl.
CPC .............. *G06T 7/0008* (2013.01); *G06T 7/62* (2017.01); *G06T 7/90* (2017.01); *H04N 5/225* (2013.01); *H04N 5/2252* (2013.01); *H04N 5/2253* (2013.01); *H04N 7/185* (2013.01); *B64C 2201/027* (2013.01); *B64C 2201/12* (2013.01); *G06K 2209/17* (2013.01); *G06T 2207/10024* (2013.01); *G06T 2207/10032* (2013.01); *G06T 2207/10056* (2013.01); *G06T 2207/20081* (2013.01); *G06T 2207/30128* (2013.01); *Y02A 50/30* (2018.01); *Y10S 901/01* (2013.01); *Y10S 901/09* (2013.01); *Y10S 901/40* (2013.01); *Y10S 901/41* (2013.01)

(56) References Cited

U.S. PATENT DOCUMENTS

| | | | |
|---|---|---|---|
| 9,867,511 B1* | 1/2018 | Wilburg | A47K 11/023 |
| 9,877,783 B2* | 1/2018 | van der Weide | A61B 18/1815 |
| 9,891,110 B1* | 2/2018 | Pei | G01J 5/026 |
| 9,967,924 B2* | 5/2018 | Heczko | H05B 6/1245 |
| 10,156,036 B2* | 12/2018 | Bush | D06B 1/02 |
| 2001/0019051 A1* | 9/2001 | Clothier | H05B 6/06 219/622 |
| 2004/0081221 A1* | 4/2004 | Sandvoss | G01N 25/72 374/130 |
| 2008/0014111 A1* | 1/2008 | Hedman | A61L 2/16 422/3 |
| 2008/0147056 A1* | 6/2008 | van der Weide | A61B 90/37 606/33 |
| 2009/0000620 A1* | 1/2009 | Virr | A61M 16/142 128/203.27 |
| 2010/0024462 A1* | 2/2010 | Kamisako | A23L 3/363 62/331 |
| 2011/0064605 A1* | 3/2011 | Hedman | A61L 2/06 422/3 |
| 2011/0064607 A1* | 3/2011 | Hedman | A01M 19/00 422/5 |

* cited by examiner

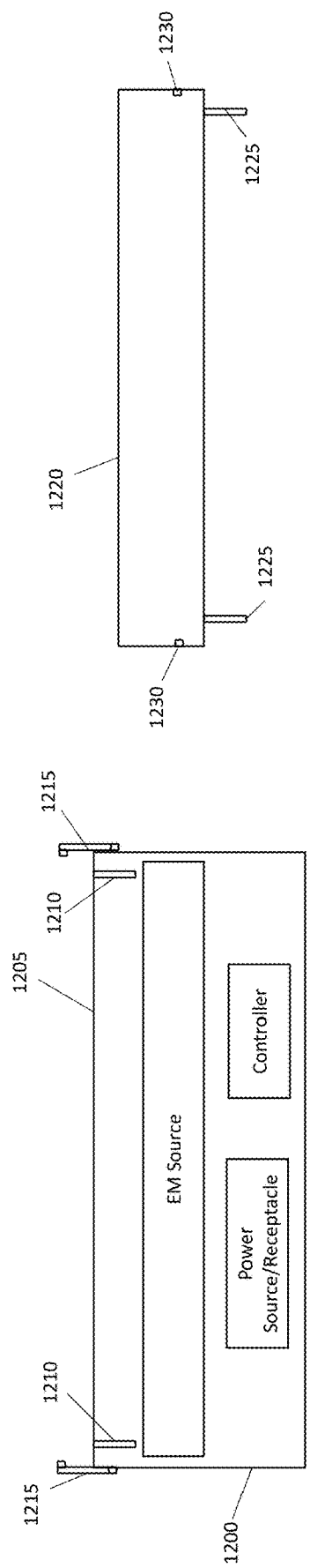

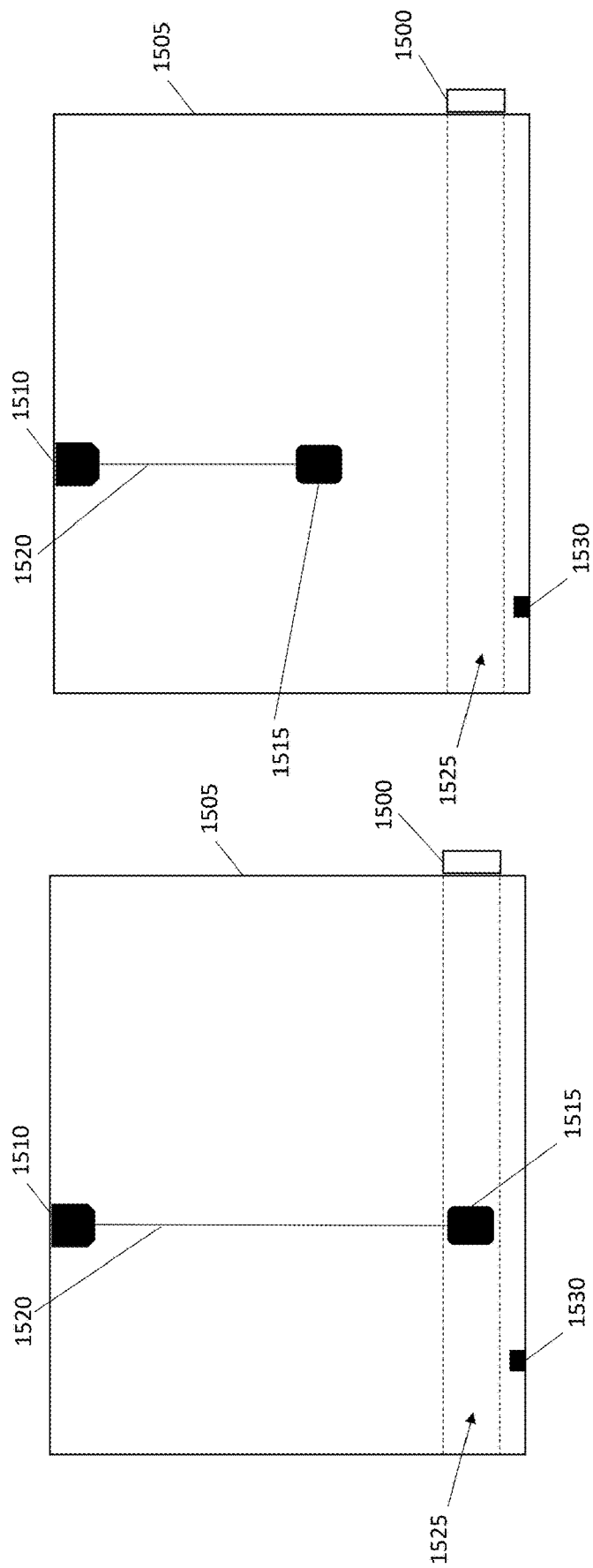

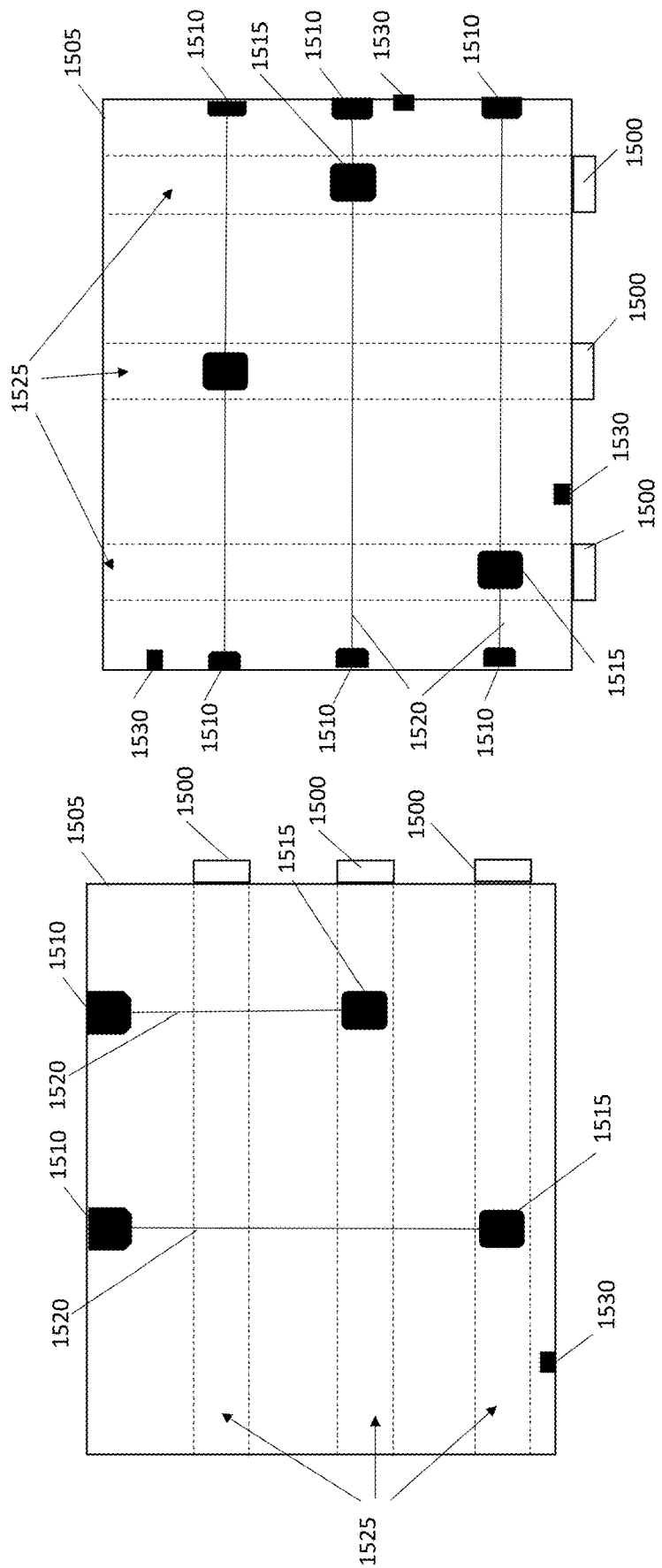

INDUCTION HEATING SYSTEMS

CROSS-REFERENCE TO RELATED APPLICATIONS

The present application claims priority as a continuation application of U.S. patent application Ser. No. 16/891,267 filed on Jun. 3, 2020, which is a continuation-in-part of U.S. patent application Ser. No. 16/575,907, filed on Sep. 19, 2019, which is a continuation-in-part of U.S. patent application Ser. No. 16/393,445 filed on Apr. 24, 2019, which is a continuation-in-part application of U.S. patent application Ser. No. 16/238,602 filed on Jan. 3, 2019, which is a continuation-in-part application of U.S. patent application Ser. No. 16/100,489 filed on Aug. 10, 2018, which is a continuation-in-part application of U.S. patent application Ser. No. 16/035,919 filed on Jul. 16, 2018, which is a continuation-in-part of U.S. patent application Ser. No. 15/956,083 filed on Apr. 18, 2018, which is a continuation-in-part application of U.S. patent application Ser. No. 15/919,541 filed on Mar. 13, 2018, which is a continuation-in-part application of U.S. patent application Ser. No. 15/802,814 filed on Nov. 3, 2017, which claims priority to U.S. Patent App. No. 62/551,345 filed on Aug. 29, 2017. U.S. patent application Ser. No. 15/802,814 is also a continuation-in-part of U.S. patent application Ser. No. 15/654,390 filed on Jul. 19, 2017 (now U.S. Pat. No. 9,852,362), which is a continuation-in-part of U.S. patent application Ser. No. 15/425,079 filed on Feb. 6, 2017 (now U.S. Pat. No. 9,811,764), which is a continuation of U.S. patent application Ser. No. 15/153,621 filed on May 12, 2016 (now U.S. Pat. No. 9,563,945), which claims priority to U.S. Patent App. No. 62/183,591 filed on Jun. 23, 2015. U.S. patent application Ser. No. 15/153,621 is also a continuation-in-part of U.S. patent application Ser. No. 14/733,044 filed on Jun. 8, 2015 (now U.S. Pat. No. 9,381,646), which is a continuation-in-part of U.S. patent application Ser. No. 14/505,430 filed on Oct. 2, 2014 (now U.S. Pat. No. 9,053,528), which is a continuation-in-part of U.S. patent application Ser. No. 13/542,416 filed on Jul. 5, 2012 (now U.S. Pat. No. 8,855,374), which claims priority to U.S. Patent App. No. 61/504,462 filed on Jul. 5, 2011. Each of these priority applications is incorporated herein by reference in their entirety.

BACKGROUND

The decreased use of pesticides on the one hand and the decreased effectiveness of those which are in use on the other, has resulted in a disturbing proliferation of insects in food and in the home. Moreover, insects and other invading offending objects frequently infest orchards or similar crops, which can cause crop damage and decreased yields. Other types of offending objects can include aircraft such as drones that are used for spying and planning military operations. Some drones have been designed to include firearms that are used to attack targets in military zones. Additionally, offending objects can include undetonated explosives which can cause serious injury and death in post-war zones.

SUMMARY

In one embodiment, described herein is a computer image analysis system, which captures an image of a substrate or other area to be checked for offending objects and is trained to recognize various offending objects commonly associated with such substrates to be checked. If an offending object is identified any of various action operations are taken in different embodiments described herein, including removal of the offending object by way of an action head associated with an imaging device. Another action operation can include destroying the offending object by the action head. In some embodiments, the system is positioned on a movable platform to scan a wide area for offending objects and/or to perform mitigation actions once an offending object is detected.

An illustrative device for use in identifying an explosive includes a processor and an induction heat source in communication with the processor. The induction heat source is configured to emit radiation to heat a metallic component of an explosive device by way of induction. The device also includes a temperature sensor in communication with the processor that is configured to detect heat emitted from the metallic component of the explosive device. The processor is configured to identify a location of the metallic component of the explosive device based on the detected heat. The device further includes an action arm configured to conduct a detonation attempt at the location of the metallic component of the explosive device. A gas sensor of the device is used to detect one or more gases emitted from a non-metallic explosive device.

An illustrative method for detecting explosives includes emitting, by an induction heat source of a detection device, radiation to heat a metallic component of an explosive device by way of induction. The method also includes detecting, by a temperature sensor of the detection device, heat emitted from the metallic component of the explosive device. The method also includes identifying, by a processor in communication with the induction heat source and the temperature sensor, a location of the metallic component of the explosive device based on the detected heat. The method further includes conducting, using an action arm of the detection device, a detonation attempt at the location of the metallic component of the explosive device.

An illustrative device for use in detecting metallic objects includes a processor and an electromagnetic radiation source in communication with the processor. The electromagnetic radiation source is configured to emit radiation to heat a metallic object. The device also includes a temperature sensor in communication with the processor. The temperature sensor is configured to detect heat emitted from the metallic object. The device also includes an alarm configured to notify an operator of the presence of the metallic object responsive to a determination by the processor that a temperature threshold has been exceeded.

An illustrative method for detecting metallic objects includes emitting, by an electromagnetic radiation source of a detection device, radiation to heat a metallic object by way of induction. The method also includes detecting, by a temperature sensor of the detection device, heat emitted from the metallic object. The method also includes determining, by a processor of the detection device, whether the heat emitted from the metallic object exceeds a temperature threshold. The method further includes triggering an alarm responsive to a determination that the temperature threshold is exceeded.

An illustrative mold remediation system includes a processor and an electromagnetic radiation source in communication with the processor. The electromagnetic radiation source is configured to emit radiation to heat a ferromagnetic material in or adjacent to a wall board upon which mold is located. The system also includes a temperature sensor in communication with the processor. The temperature sensor is configured to detect a temperature of the wall board. The processor is configured to compare the temperature of the wall board to a desired temperature to perform mold remediation.

An illustrative method for performing mold remediation includes emitting, by an electromagnetic radiation source, radiation to heat a ferromagnetic material in or adjacent to a wall board upon which mold is located. The method also includes detecting, by a temperature sensor, a temperature of the wall board. The method further includes comparing, by a processor in communication with the electromagnetic radiation source and the temperature sensor, the temperature of the wall board to a desired temperature to perform mold remediation.

An illustrative induction heating system includes a base having a controller and an electromagnetic radiation source in communication with the controller. The electromagnetic radiation source is configured to emit radiation. The base also includes a mounting surface configured to receive one of a plurality of interchangeable heating surfaces. The system further includes a heating surface mounted to the mounting surface of the base. The heating surface includes a ferromagnetic material that heats via induction responsive to the radiation emitted by the electromagnetic radiation source.

Another illustrative induction heating system includes a container that includes one or more ferromagnetic element mounting locations. The system also includes a plurality of ferromagnetic elements positioned in the one or more ferromagnetic mounting locations. The system also includes one or more electromagnetic radiation sources configured to individually target the plurality of ferromagnetic elements such that different ferromagnetic elements are heated to different temperatures. The system further includes a processor operatively coupled to the one or more electromagnetic radiation sources and configured to control an amount of electromagnetic radiation delivered to each of the ferromagnetic elements.

Another illustrative method of induction heating includes receiving, by one or more ferromagnetic element mounting locations of a container, a plurality of ferromagnetic elements. The method also includes individually targeting, by one or more electromagnetic radiation sources, the plurality of ferromagnetic elements such that different ferromagnetic elements are heated to different temperatures. The method further includes controlling, by a processor operatively coupled to the one or more electromagnetic radiation sources, an amount of electromagnetic radiation delivered to each of the ferromagnetic elements.

An illustrative induction heating system a base and an electromagnetic radiation source configured to generate an emission area in the base. The emission area comprises a portion of the base that receives electromagnetic radiation from the electromagnetic radiation source. The system also includes a ferromagnetic element and an element controller configured to move the ferromagnetic element into and out of the emission area.

Another illustrative induction heating system includes a base and an electromagnetic radiation source configured to generate an emission area in the base. The emission area comprises a portion of the base that receives electromagnetic radiation from the electromagnetic radiation source. The system also includes a ferromagnetic element. The ferromagnetic element is configured to move itself into and out of the emission area.

Other principal features and advantages of the invention will become apparent to those skilled in the art upon review of the following drawings, the detailed description, and the appended claims.

BRIEF DESCRIPTION OF THE DRAWINGS

Illustrative embodiments will hereafter be described with reference to the accompanying drawings, wherein like numerals denote like elements. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

FIG. 12A is a side view of a base unit of a portable induction heating system in accordance with an illustrative embodiment.

FIG. 12B is a side view of a heating surface that mounts to the base unit in accordance with an illustrative embodiment.

FIG. 15A is a first side view of an induction heating system with a moving ferromagnetic element in accordance with an illustrative embodiment.

FIG. 15B is a second side view of the induction heating system with the moving ferromagnetic element in accordance with an illustrative embodiment.

FIG. 15C is a side view of an induction heating system with a plurality of moving ferromagnetic elements and a plurality of EM radiation sources in accordance with an illustrative embodiment.

FIG. 15D is a side view of an induction heating system with a plurality of moving ferromagnetic elements and a plurality of EM radiation sources in accordance with another illustrative embodiment.

DETAILED DESCRIPTION

Embodiments of the present subject matter will now be described with reference to the above-identified figures. However, the drawings and the description herein are not intended to limit the scope of the invention. It will be understood that various modifications of the present description are possible without departing from the spirit of the invention. Also, features or operations described herein may be omitted, additional operations or features may be included, and/or features or operations described herein may be combined in a manner different from the specific combinations recited herein without departing from the spirit of the invention.

In one illustrative embodiment, a lens is used to point at a leaf of lettuce and capture an enlarged image thereof via an image capturing device. The image may be stored in digital memory for later analysis or it may be analyzed in real time. In either case, the image is sent to a processor that is trained to recognize the general characteristics and color of the lettuce, and which is also trained to recognize physical characteristics and features of insects typically found on lettuce. The image is magnified so that the presence of the insect, even if well hidden, will be identified by comparison with a library of insects stored in memory. In one embodiment, the processor does not positively identify a bug or other identifiable foreign object, but it may recognize the object as foreign. For instance, a processor may contain parameters of acceptable color values or hues for a specific substrate and if an object is outside of such parameters—software running on the processor determines the object as "foreign."

The identification of the insect can immediately trigger a response in an action head which is attached to the lens housing and is capable of moving to the insect position, and removing or destroying the insect automatically. In another embodiment, rather than removing an observed insect—an action head grips the piece of lettuce and discards it.

Figure 1:
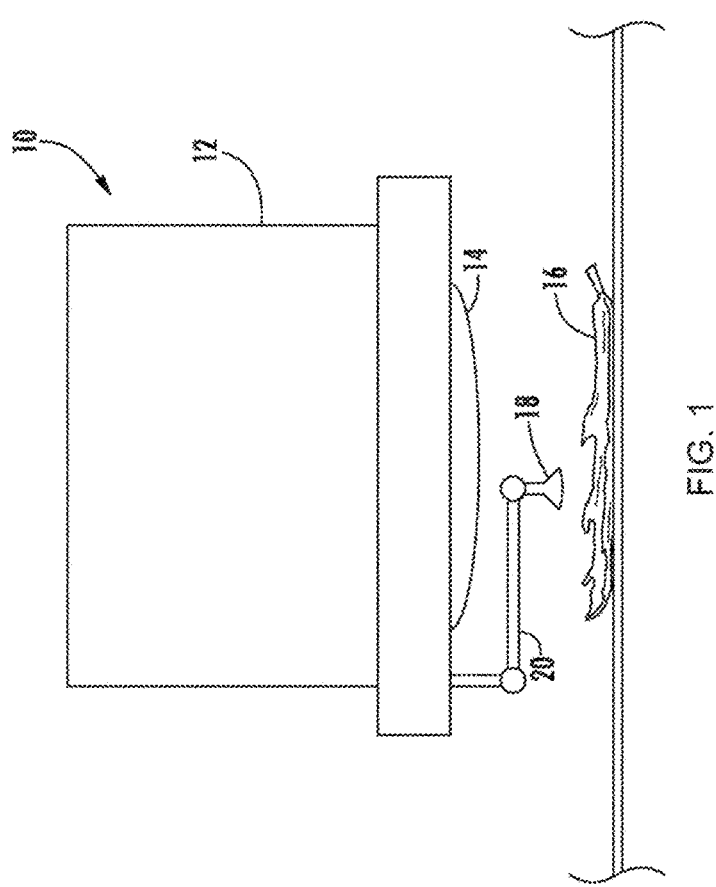
FIG. 1 shows a schematic side view of a scanning device disposed above a substrate to be checked according to an illustrative embodiment.

FIG. 1 shows a scanning device having a casing 12, which houses an image recognition system. A downward facing microscope, lens 14 or any such image capturing device and magnification device is located at a bottom portion of the scanning device. As shown, the lens 14 is directed at a substrate 16, such as, for example, a piece of lettuce. The lens magnifies a segment of a substrate to be checked and it feeds captured images to an image recognition system for image analysis. Images may be stored on a digital storage medium, among other storage systems or media.

It will be understood by those of ordinary skill in the art that the device 10 may be provided with a plurality of differently powered lenses which may be automatically adjusted when greater focusing ability is needed and any of different image capturing devices may be utilized, such as for example, a camera or a video camera, a video telescope, a video monocular, or an array thereof. It should also be understood that the image recognition system need not be housed within the casing 12 of the device—but rather the image recognition software may be provided at a location that is distant from the image-capturing device. In such embodiment, an image-capturing device (e.g. a microscope lens coupled to an image capturing system) is utilized to capture images. The images are then sent by a wired or wireless connection to an image classifier.

FIG. 1 shows an action head 18, which is provided at the distal end of a movable arm 20. The action head may be equipped with one or more instruments, such as a gripping device and/or a suctioning device. In another embodiment described herein, the action head is provided with a heating element or similar heat source—which can destroy a bug or a segment of lettuce when it is brought into direct contact therewith.

In one embodiment, the device 10 housing the lens 14 and action head 18 is a handheld unit, which may be manually or automatically moved across a stationary substrate such as a leaf of lettuce. In another embodiment the device 10 is mounted on a stationary support structure and a conveyor belt positioned below the device delivers items to be scanned below the microscope lens of the device. Still in other embodiments, the device is mounted to a linear motion track and it incrementally moves (for instance by incremental movements of a rack and pinion wheel controlled by a computer) across a substrate to be searched. In one embodiment, the device 10 may be used for purposes of "surveillance." In this embodiment, the device is mounted in a fixed position. When an offending object (such as an insect) enters the field of vision of the lens and is recognized as such by the image recognition system—a command is sent to activate the action head 18 to eliminate and/or neutralize the offending object. It is to be understood that as an alternative to eliminating and/or neutralizing an offending object, the device could mark the offending object for subsequent removal or remedial action. In some embodiments, device 10 may be a drone, which may be a remotely controlled and/or autonomously controlled vehicle (e.g., aircraft, ground vehicle). For example, an autonomous vehicle may be operated according to pre-programmed rules, such as navigation directions (e.g., coordinates or street directions), and/or logical rules to govern operation, such as obstacle avoidance rules and/or task execution rules (e.g., using a scanning or imaging device to assess various subjects).

It should be further understood that the moveable arm described herein may be its own detached unit, but which operates under the control of the software, which software may be stored in memory on the device 10 and configured to run on one or more processors, or which software may be remotely located, such as on a remote server accessible via a data communication signals and/or data networks. An illustrative device control system is described herein with reference to FIG. 4.

In an illustrative embodiment, action head 18 is mounted on an exterior surface of a device such as a drone, a vehicle, or the like. In other embodiments, action head 18 is attached to the distal end of a movable arm. It will be understood that a movable arm may be any of various structures such as, for example, one or more linear guide tracks, rack and pinion systems or such similar relative motion mechanism for supporting and moving an action head. The arm is movable in any of various directions by way of ball joints, linear motion tracks or other such similar movement systems. When a bug or other offending object is detected by the image recognition system, the software is programmed to send a signal to the moveable arm. The moveable arm is then controlled by a software application and directed to the located bug. The action head is deployed to either destroy the bug as described above or to suction it off of the substrate. In one embodiment, rather than directing the action head to a specific location—the moveable arm is directed to push the piece of lettuce (or other substrate) away, thereby discarding the same or removing it from a batch.

The computer used to control operations, execute routines and store data may include at least one or more processors and memory storage devices. The computer also may receive a number of inputs and outputs for communicating information externally.

It is to be understood that the computer which operates the device may operate under the control of an operating system and software applications, components and programs that execute the routines and systems described herein. In general, the routines executed to implement the embodiments, whether implemented as part of an operating system or a specific application, component, program, object, module or sequence of instructions will be referred to herein as "the system", or "software". The software controls the image acquisition, image storage, image analysis and movements of the arm, action head and/or the movement of the device along a track.

It is further to be understood by those of ordinary skill in the art that the described apparatus can include image capturing capabilities and image recognition capabilities coupled with software that is programmed to determine whether or not an object in an image field is an offending object. An "offending object" herein is any physical, identifiable structure or shape that is targeted for action. Examples of offending objects may include, but are not limited to, stationary insects, dirt, mold growth, plant features, product imperfections, drones, flying insects, etc. The device is programmed to take an action once an offending object is detected. "Action" can refer to any remedial steps taken by the device to eliminate or otherwise address the offending object. For example, in one embodiment, the action head 18 of device 10 advances to a location of an offending object and it records the spatial coordinates of the same. The coordinates are stored for later treatment and or elimination.

Figure 2:
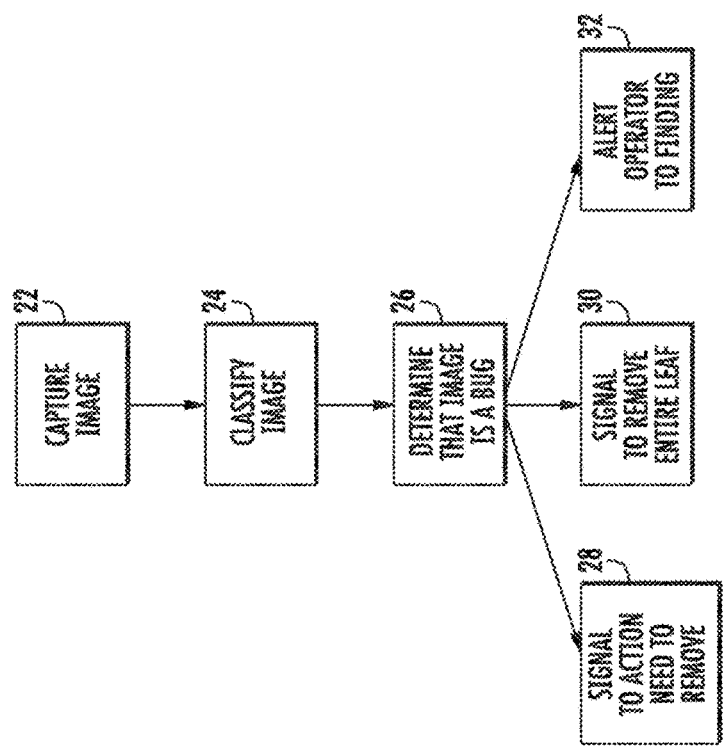
FIG. 2 is a flow chart showing software processing operations according to an illustrative embodiment.

FIG. 2 shows a number of processing steps performed by the software in accordance with an illustrative embodiment. The device is initiated and begins capturing images 22. The images are sent to an image recognition system which classifies various images 24. The classifier may be an algorithmic classifier or a neural network system. The image recognition system is trained to recognize morphological/physical characteristics of bugs or other objects to be detected. The image recognition may also be trained to detect pixel concentrations which may indicate the presence of bug or other objects of interest.

If an image is determined to be a bug 26, then the software performs further processing operations. In one embodiment, the software sends a signal to the moveable arm 28, which directs the action head to the location of the bug to remove the same according to the teachings described above. In another embodiment, the software sends a signal to the moveable arm to push aside the item 30 upon which the bug was detected. Still in another embodiment, upon detecting a bug, the software sends or sounds an alert to a human operator 32. The human operator may intervene to remove the bug or the item.

In another illustrative embodiment, the device can be specifically designed to deal with only one kind of insect on one kind of food or other material, or one other type of offending object. A single kind of action suitable for the situation can be built into such a device.

Extension to a more sophisticated device can be implemented with software taught to deal with many different kinds of foods and materials, to recognize a range of different insects or objects, and different means of removing the insect, including a vacuum, a glue head, an electrical charge, freezing, heat, or even a drop of powerful insecticide. Powerful pesticides sprayed or deposited over a large area are harmful, but a targeted drop on the insect itself will dispatch the insect and not significantly affect the surrounding atmosphere.

In another embodiment, the system can include an array of lenses and response heads so that a sheet being inspected for bed bugs can be continuously passed under the array.

In another embodiment, the system may be used to remove offending objects, such as bugs, from a fluid. In one embodiment, an image capturing device is fixed above a channel of flowing liquid. The device may include an array of image capturing devices or lenses suspended above a channel or similar fluid stream. It will be understood that in one embodiment, the action head may be a vacuum head or suction head such that when the image recognition system detects a presence of an offending object, the software sends a command to the action head to vacuum an area of fluid in the vicinity of the offending object. The vacuum head or suction head can then draw in the offending object, and possibly, some of the surrounding fluid and discard the same.

The present system may be used in any of various environments in which subtle changes need to be detected and then acted on. For example, the beginning of a disease affecting trees or other plants and its subsequent spread is often the result of an insect, beetle or bug penetrating the bark or other surface and destroying the structure from within. Detecting a presence of a specific kind of invader is virtually impossible if it requires a human observer's continued close observation. The instant embodiments can be deployed in a manner which detects and acts whenever an invader is detected on the surface. For example, the software may be trained to detect specific bugs or locusts. Once detected, the software sends a command to spray an offending substance or a pesticide.

In another embodiment, the software is programmed to detect swarms of bugs or other flying objects—irrespective of the type of bugs or objects. In one example, the software is trained to detect a plurality of distinct moving objects within an area of interest. Once a threshold number of moving objects (e.g. >10) is detected, the software will confirm a presence of a swarm and it will automatically send instructions to the action head to address the swarm. In one embodiment, the action head will spray a mist of water vapor or insecticide, smoke laced with insecticide, repellant or similar offending substances. Alternatively, the device can be configured to sound an alarm to disperse the swarm.

The system described herein can be modified to recognize the sign of incipient disease on the skin of a human being at a size that is invisible or almost invisible to the human eye. It is evident that the principles of the proposed systems can be readily applied to other areas where detection, recognition, and action upon a flaw, intrusion, or incipient flaw at a stage where it is barely visible.

Depending on the specific use, the described systems can be associated with a variety of platforms, both mobile and stationary. For example, the image capturing lens and action head may be mounted to a movement mechanism such as a linear guide track, a pulley system, a rack and pinion or any such similar movement mechanisms. Alternatively, the device may be attached to or embedded within a drone, hovercraft, aircraft or similar dirigible. (Mechanical devices/ mechanisms for moving the device can be referred to as "movable platforms" herein.) In one in which the device is mounted to a movement mechanism, the software may be programmed to move the device in any of various predetermined or random movements. In such an embodiment, once an offending object is detected, the software sends a command to interrupt movement of the device and deploy the action head to execute one or more remedial actions.

Control of any of the mobile or active platforms envisioned above can be implemented in a variety of ways, including voice recognition. Additionally, the devices and systems described herein, as well as any attendant platform or support, can be supplied with energy in a variety of ways, including batteries, solar, electromagnetic and hard wires, among others.

The proposed systems and devices are not limited to any specific materials of construction or size, and are readily modified by change in programmed recognition patterns to react to different insects, insect parts, plants, plant parts, flying objects, and in some embodiments, to detect extremely small predictable defects or imperfections, among others, in the manufacturing process or in manufactured products. In this latter use, more than one device can be connected to work in tandem, or in any manner called for by the situation.

In one embodiment, the device is furnished with assisted illumination to extend its use at night, through the use of light and infrared, among others. To extend its use further, x-ray and other surface penetrating radiation can be attached to the platform or to the device itself. The image recognition and instant response features of the system can also be incorporated into or provided on the platform.

In one embodiment, a robot platform or movable platform may be provided with an image magnification device to magnify an image of an area, segment and/or substrate to detect objects it is trained to detect.

It is to be understood that in addition to observing and capturing images, the robot or movable platform may be programmed to provide an active response to remove, mitigate and/or react to various conditions. Any of a variety of actions may be deployed by the robot such as, but not limited to, sending an alert or an update, and/or expelling a spray or substance such as pesticide, vapor or smoke. For example, in some embodiments a movable platform such as a robot, vehicle, or drone is utilized to travel about a field, orchard or forest and obtain images of plants and/or trees growing therein. The software detects any of various conditions associated with plants and/or trees and is trained to react accordingly. In one embodiment, the device is trained to detect boring insects (e.g. Emerald Ash Borers) by recognizing physical features such as appearance, color, size, shape etc. Additionally or alternatively, the device detects holes in plants or trees created by such insects. The device then automatically responds by directing the action arm to the detected insect or its entry hole. For example, in one embodiment, the device directs the action arm to an entry hole formed by boring insects and releases a blast of white paint or similar marking material to mark the tree for removal or for remedial treatment.

In a further implementation, the device is programmed to provide an instant response which results in recognition and capture instead of recognition and reject. That is, objects, such as insects, which are of interest instead of being offending, can be trapped and captured with the same device, using only a modification. That is, rather than dispersing or deflecting an object of interest, the software sends a signal to the mechanical arm to capture and maintain the object of interest.

The device may also be deployed for use in quality control activities. In this embodiment, the device may be trained to recognize qualitatively acceptable objects and those that do not meet acceptable criteria (or "defective objects"). The software is programmed to employ an action head to capture defective objects. Acceptable criteria may be any of size criteria, shape criteria or such similar metrics calculated by the software or algorithmic classifier. In other embodiments, acceptable criteria may be based on color criteria, pixel counts, pixel saturation or any such similar image criteria the software and image recognition/analysis software is programmed to analyze.

The devices and systems described herein can also be used as a stand-alone, hand held devices, or devices that are fixed in place with items to be inspected passing through. In one embodiment, the lens/image capture device and action heads can be in a circular or other convenient pattern, and on both sides of the material, as on both sides of a sheet.

In one embodiment, the proposed device is attached to a drone which is programmed to move up and down, and all around a tree periodically, and subsequently to move on to other trees. This will enable the device to protect forests, orchards, and plantations against invasive species. Drones can be programmed to travel in certain sectors of a forest or orchard, around a periphery or in any pattern as designated by an operator to capture images in the area below it and instantly react.

A drone can also be programmed to remain stationary, detecting and protecting against the arrival of an expected invasive species for which it has been trained. Similarly, attaching the device to a robot enables the protection against land based invasive species in addition to airborne species.

In each case, the proliferation of robots and drones, as well as other platforms, extends the use and effectiveness of the device. Included in such other platforms are hovercrafts, extendable legs and floatable devices among others known to those skilled in the art.

Figure 3:
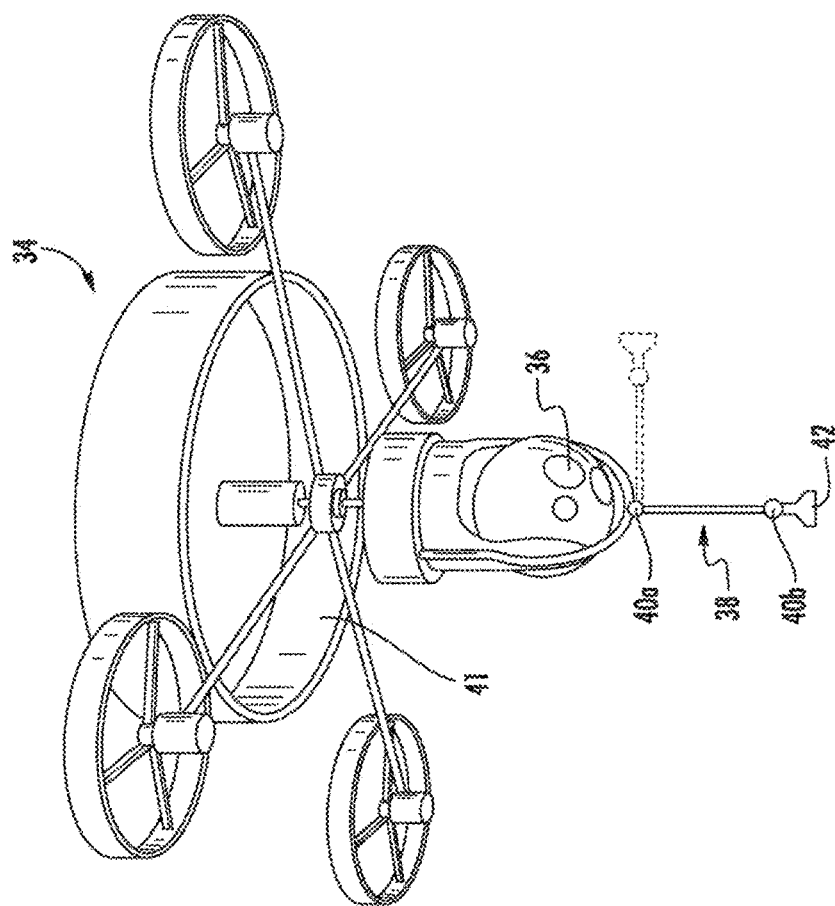
FIG. 3 shows a side perspective view of a scanning device incorporated with a drone according to an illustrative embodiment.

FIG. 3 shows a drone 34 used to capture images and provide an active response according to an illustrative embodiment. Drone 34 has an image capturing device for capturing images of areas to be analyzed. For example, as shown, drone 34 has a lens 36 which is part of a camera or video camera. In one embodiment, the image capturing device is housed in a movable and/or rotatable housing. The lens 36 captures images, which are then analyzed by the image analysis software. The image analysis software may be located in a computer residing in the drone 34 or images may be sent via wire or wireless communication to a computer at another location.

An action arm 38 is shown extending from the body of the drone 34. Action arm 38 has one or more rotatable joints 40a, 40b, ball joints or similar pivoting members allowing for various movement of the action arm 38. For example, in the embodiment shown, action arm 38 is shown pointing downward in an orientation substantially orthogonal to the body 41 of the drone, but it could be rotated around joint 40a to a 90.degree. angle.

An action head 42 is shown positioned at the terminal end of action arm 38. The software is configured to direct action head 42 in the direction of a detected offending object and to automatically initiate remedial actions. For example, action head 42 is activated to expel any of various substances described above in response to a command from the software. A tank or similar storage reservoir within the drone stores substances to be dispersed or dispensed from the drone.

In another embodiment, drone 34 is used to capture images of plants or features of plants and to disperse pollen in response to such detection. In some embodiments, the system detects images of plants such as flowers and trees to determine whether or not the plant is a flowering plant adapted for receiving pollen. Additionally or alternatively, the system detects plant objects or features that are adapted to receiving pollen. Upon detection of such plants and/or upon the detection of reproductive features of flowering plants—the drone automatically dispenses pollen. In one embodiment, the pollen is directed to the approximate location of detected flowering plants, but in other embodiments, the pollen is directed to an area proximate to a detected flower or reproductive feature.

In an illustrative embodiment, an image capturing mechanism is used to capture images of plants, trees or other vegetation and image analysis software is utilized to detect objects consistent with flowering plants. As will be understood by those of ordinary skill in the art, the image analysis software may be located in a computer residing in the drone 34 or images may be sent via wire or wireless communication to a computer at a remote location. The image analysis software determines whether or not a plant is one that is adapted to receive pollen and/or whether or not a plant feature is an organ that is adapted to receive pollen (such as a pistil).

In some embodiments, the drone 34 may be directly controlled by a human operator, whereas, in other embodiments the drone is controlled by one or more computers. The drone 34 flies over areas of vegetation and its image capturing system scans the terrain below. In some embodiments, as described above, the image analysis system is trained to detect specific plants for purposes of pollination. In other embodiments, the image analysis system is additionally or alternatively trained to detect specific plant features that are adapted for receiving pollen.

In another illustrative embodiment, once a particular plant-type is detected, the system is programmed to release pollen in the vicinity of such detected plants. That is, once a plant of interest is detected, the software sends a command to the drone to navigate toward such plants and to release pollen.

In other embodiments, the system is programmed to detect specific plant features, like pistils. Once a pistil is detected, the program sends a command to an action arm to release pollen in the direction of the detected pistil. Action arm 38 is shown extending from the body of the drone 34. Action arm 38 has one or more rotatable joints 40a, 40b, ball joints or similar pivoting members allowing for various movement of the action arm 38. For example, in the embodiment shown, action arm 38 is shown pointing downward in an orientation substantially orthogonal to the body of the drone, but it could be incrementally rotated around joint 40a to a 90 degree angle in order to more accurately point the action head 42 in the direction of a pistil.

Action head 42, shown positioned at the terminal end of action arm 38, is provided with a nozzle or such similar spout for releasing a cloud, mist or similar stream of pollen. The software is configured to direct action head 42 in the direction of a flower to be pollinated and automatically expel pollen in the direction of the plant of interest, flower of interest, or plant feature of interest. A tank or similar reservoir within the drone stores substances to be dispersed or dispensed from the drone.

In one illustrative implementation, the system is programmed to detect features associated with almond trees. In this embodiment, once the software confirms a presence of an almond tree, it will automatically send instructions to navigate the drone 34 to an area proximate to the almond tree and subsequently send instructions to the action head 42 to release pollen. In one embodiment, the software is trained to identify flowers on almond trees and to disperse pollen on or near respective flowers. In other embodiments, the system is trained to detect respective reproductive features on flowers of the almond tree (such as pistils) and the action arm is instructed to direct the action head 42 toward the reproductive features. Once the action head is properly oriented, a command is sent to expel a spray or mist of pollen.

In another illustrative embodiment, the software is trained to recognize a specific pistil and initiate a dispersal of pollen that is specific to the pistil of interest. In another embodiment, reservoirs of different pollen types are provided on the drone or similar movable device. The software is trained to recognize and detect a variety of different flowers/pistils (associated with different flowers or flower types) and disperse a pollen type that corresponds to the detected pistil.

It will be understood by those of ordinary skill in the art that drone 34 or a similar aircraft, hovercraft or dirigible having an image capturing device in communication with an image recognition system may be used to detect and monitor any of various conditions and instantly react by dispersing any of various substances or performing other actions via an associated action head. For example, a device may be programmed to detect plant conditions or soil conditions (e.g. using color properties thereof) and to automatically disperse water or nutrients to the detected areas when a dry soil condition or an unhealthy plant condition is detected. In other embodiments, a device may be programmed to detect fires. For example, a drone may be programmed to fly over a forested area and detect visual indicia of smoke or fire. Additionally or alternatively, the device may have a heat sensor to detect fires. Once a fire is detected, the device is programmed to navigate into proximity of the fire and automatically disperse fire retardants such as chemicals or water.

In an illustrative embodiment, the computer which operates the device may operate under the control of an operating system and software applications, components, and programs that execute the routines and systems described herein. In general, the routines executed to implement the embodiments, whether implemented as part of an operating system or a specific application, component, program, object, module or sequence of instructions will be referred to herein as "the system", or "software". The software can control the image acquisition, image storage, image analysis and movements of the arm, action head and/or the movement of the device along a track or other movement mechanism.

Figure 4:
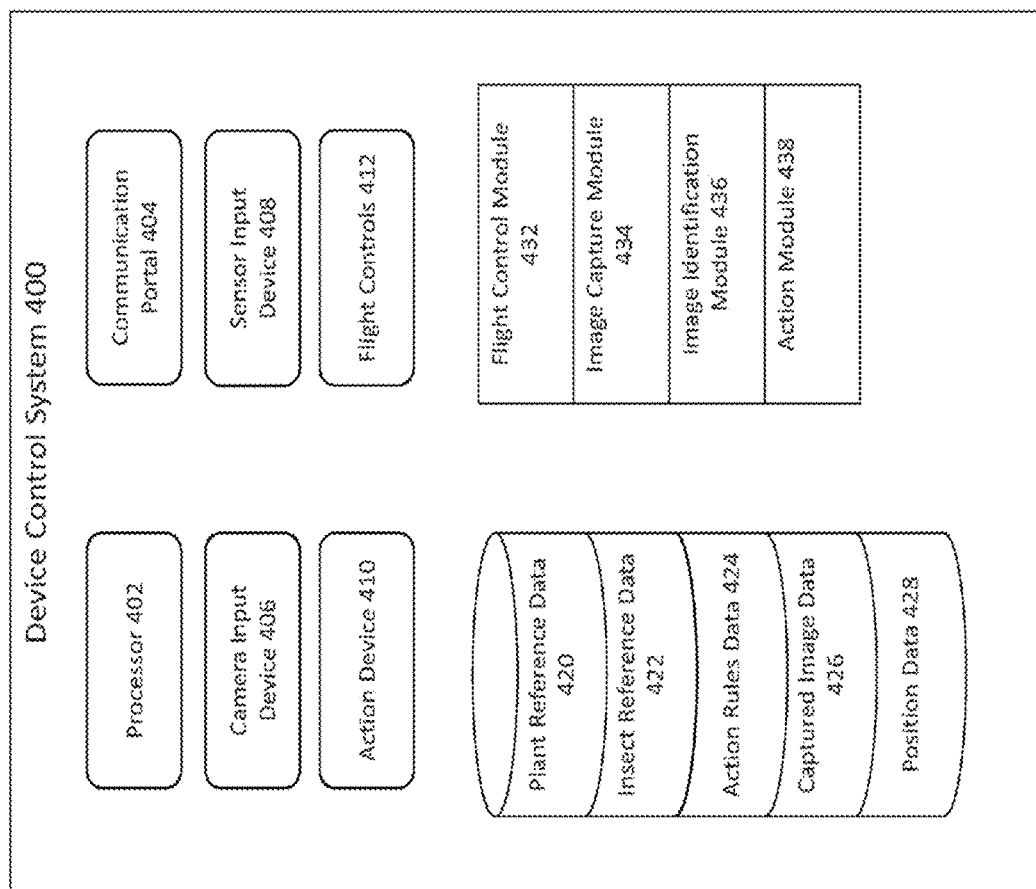
FIG. 4 is a schematic diagram of a device control system according to an illustrative embodiment.

FIG. 4 is a schematic diagram of a device control system 400 in accordance with an illustrative embodiment. The device control system may include a computer system having one or more computers. The device control system may govern operation of an imaging and/or image evaluation device, as may be employed by an imaging drone as described herein. In some embodiments, certain components of the device control system 400 may be located on-board the device, such as on or within a drone, or remotely, such as at a remote computer system, which may be accessible via a data network. For example, the image identification module 436 and/or action module 438 may be located remotely, e.g., on one or more servers. Image data may be uploaded (via physical connection of memory storage devices and/or wirelessly) to the image identification module 436 for evaluation. In some embodiments, action instructions may be transmitted by an action module 438 to one or more drones for execution.

The device control system 400 may include hardware, such as one or more processors 402, a communication portal 404, one or more camera input devices 406, one or more sensor input devices 408 (e.g., scanners, range finders, position sensors (e.g., GPS receivers, altitude sensors, to name a few)), action device 410 (e.g., action head and/or movable arm, as described herein), and/or flight controls 412. Flight controls 412 can include thrusters, engines, motors, turbines, fans, rotors, propellers, thrust vectoring control surfaces, aerodynamic control surfaces, and/or actuators and/or servo motors to move such hardware components. In some embodiments, a drone can include wheels, treads and tracks, or other ground propulsion systems, including motors. In other embodiments, the drone can be designed to float and thus may include floatation devices (e.g., pontoons) or buoyant exterior components of the drone, as well as a water propulsion system.

The device control system 400 may further include non-transitory computer-readable memory (e.g., local and/or remote), which may store and/or access data, e.g., in one or more databases. Such data can include plant reference data 420, insect reference data 422, action rules data 424, captured image data 426 or other sensor data, and/or position data 428, as described herein. The device control system 400 may also include one or more software modules stored in the memory and configured to execute machine-readable instructions to perform one or more processes. Such modules can include a flight control module 432, image capture module 434, image identification module 436, and/or action module 438. The processes and functions described with respect to each module may be performed by one or more other modules, such as other modules described herein or additional modules.

The communications portal 404 may handle, process, support, and/or perform wired and/or wireless communications, such as transmitting and/or receiving data (e.g., data packets). In embodiments, transmission described with respect to a single data packet may comprise a plurality of data packets. Data packets may be discrete electronic units of data. In other embodiments, transmissions may comprise non-discrete signals, such as data streams. Transmissions described with respect to data packets may also comprise data transmissions via other communications mechanisms known in the art, such as data streams. Communications portal 404 can comprise hardware (e.g., hardware for wired and/or wireless connections, such as communications chipsets, communications interfaces, and/or communications antennas, to name a few) and/or software.

Wired connections may be adapted for use with cable, plain old telephone service (POTS) (telephone), fiber (such as Hybrid Fiber Coaxial), xDSL, to name a few, and wired connections may use coaxial cable, fiber, copper wire (such as twisted pair copper wire), and/or combinations thereof, to name a few. Wired connections may be provided through telephone ports, Ethernet ports, USB ports, and/or other data ports, such as Apple 30-pin connector ports or Apple Lightning connector ports, to name a few.

Wireless connections may include cellular or cellular data connections and protocols (e.g., digital cellular, PCS, CDPD, GPRS, EDGE, CDMA2000, 1.times.RTT, Ev-DO, HSPA, UMTS, 3G, 4G, 5G, and/or LTE, to name a few), Bluetooth, Bluetooth Low Energy, Wi-Fi, radio, satellite, infrared connections, ZigBee communication protocols, to name a few. Communications interface hardware and/or software, which may be used to communicate over wired and/or wireless connections, may comprise Ethernet interfaces (e.g., supporting a TCP/IP stack), X.25 interfaces, T1 interfaces, and/or antennas, to name a few.

Turning to the data that the device control system 400 may store and/or access, plant reference data 420 can include one or more images of each of a plurality of species for image comparison purposes and/or an identifier or database association to indicate the respective species associated with each image. In embodiments, the plant reference data can include images of plant parts, such as a pistil, petal, or leaf, to name a few. Plant reference data can also include growing condition data, which may be coupled with GPS data of captured images to narrow the number of reference images that are likely to produce a match. Growing condition data can include any of water availability, soil type, temperature information (e.g., temperature ranges), climate, geographic location information, etc.

Insect reference data 422 can include one or more images of insects of various species or insect components (e.g., wings) and an indicator or reference to associate each image with its respective species. Insect reference data may include size information (e.g., cross-sectional measurements, measurements of body components, such as body segments, antennas, legs), body information (e.g., number of body segments, number of antenna), color information, geographic information (e.g., indicating where the insect is likely to be found), habitat information (e.g., indicating habitats in which the insect is likely to be found, such as they type of crops, type of terrain, temperatures), and/or food source information.

Action rules data 424 can comprise rules to control an action device 410 (e.g., to control movement and/or usage of the action device 410) and/or logical rules to govern when to use the action device 410.

Captured image data 426 can comprise one or more images (e.g., image files), sequences of images, and/or videos (e.g., video files). Captured image data 426 may be associated with position data indicating a position of the subject of the image and/or a position of the drone or camera. The device control system 400 may further store and/or access additional sensor data from other sensor input devices 408, such as range information (e.g., from the drone or camera to an image subject), infrared imaging data, heat imaging data, temperature information, and/or ambient light intensity information, to name a few.

Position data 428 can include global positioning coordinates (e.g., indicating latitude, longitude, and/or altitude or elevation), street address information, and/or local coordinate information (e.g., one, two or three-dimensional locations in relation to the drone or camera).

A flight control module 432 may control movement of a drone, such as by controlling thrust, control surfaces or other flight control hardware 412.

An image capture module 434 may govern when and how to capture images (e.g., which subject to focus on, zoom level, type of imagery to capture (still versus video), and/or number of images to capture, etc.).

An image identification module 436 or image classifier may perform image analysis, such as comparisons to reference images and/or reference data as described herein, to detect one or more subjects in a captured image, such as plant species, insect species, insect quantities, and/or other foreign objects.

An action module 438 may evaluate action logical rules with respect to captured and processed image data to determine one or more actions to take. The action module may also control one or more action devices (e.g., such as an action head and/or movable arm attached thereto) to cause them to carry out the determined actions.

Figure 5:
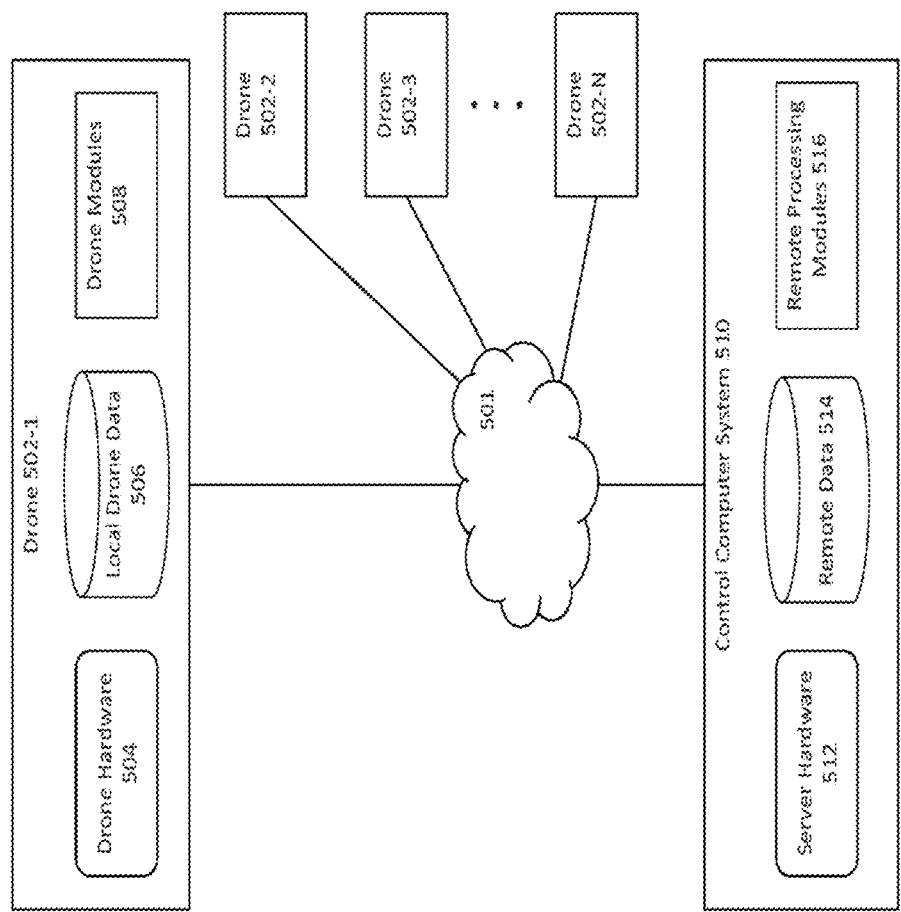
FIG. 5 is a schematic diagram of a drone scanning system according to an illustrative embodiment.

FIG. 5 shows a schematic diagram of a drone scanning system in accordance with an illustrative embodiment. The system can comprise one or more drones 502 (e.g., drones 502-1, 502-2, . . . 502-N) and/or a control computer system 510, which may be remotely located, such as on one or more servers. The devices (e.g., drones) and/or computer systems may be operatively connected directly, e.g., via wired or wireless communications, and/or indirectly, e.g., via a data network 501, such as the Internet, a telephone network, a mobile broadband network (e.g., a cellular data network), a mesh network, a local area network (LAN) (including a wireless local area network, e.g., a Wi-Fi network), a wide area network (WAN), a metropolitan area network (MAN), and/or a global area network (GAN), to name a few. Data networks may be provided via wired and/or wireless connections. Data networks may be public or private. Accordingly, data networks may be open or closed, such as requiring authorized access, specific communication connections, or specialized hardware and/or software. In some embodiments, any combination of communications channels may be utilized.

Processing of data from one or more drones 502 and/or control of each drone may be performed by one or more respective processors contained within or on each drone, one or more processors contained within or on one or more master drones that transmit commands to subordinate drones, and/or performed remotely such as at a remotely located control computer system, which may be one or more servers comprising one or more computers that receive data from and/or transmit instructions to the drones. In embodiments, any of the data processing and/or device control functions may be divided among entities, such as the drones 502 and remote control computer system 510. For example, flight controls or vehicle movement may be handled at each device, while image processing may be performed remotely. In embodiments, data acquisition may be handled at the device (e.g., capture of images and/or sensor data) and transmitted to the remotely located control computer system 510. The computer system 510 may process such data as described herein (e.g., perform image recognition and/or determine actions), and/or transmit instructions (e.g., action instructions, which may be machine-readable instructions to execute one or more determined actions) to the device 502 or to one or more other devices. Accordingly, one or more first drones 502 may acquire data while one or more second drones 502 may execute actions based upon determinations from the acquired data.

Both drones 502 and the control computer system 510 may include one or more processors, memory devices storing data in non-transitory computer-readable memory, which data may be organized in one or more databases, and communication portals (e.g., communications antennas and/or chipsets, as described herein). Drones and the control computer system may further comprise one or more input devices, e.g., to receive direct user input. Accordingly, drones may have keypads, touch screens, buttons with hardwired or programmed functionality, microphones, cameras (e.g., with gesture processing software), or other input devices. The control computer system 510 may include one or more input devices such as keyboards, mice, touchpads, touchscreens, microphones, cameras, etc., and/or output devices (e.g., display screens or speakers, etc.).

Each drone 502 may also include the respective hardware 504 (e.g., cameras, sensors, vehicle propulsion and control hardware), data 506 (e.g., rules for autonomous movement or control, flight path data, reference imagery and/or data, and/or captured data), and software modules 508 (e.g., any of the software modules described with respect to FIG. 4) to operate in such a divided control system.

Similarly, the control computer system 510 can include the hardware 512 (e.g., processors, memory devices, and/or communication portals), data 514, and/or software modules 516 running on one or more processors to perform its assigned functions. Accordingly, remote data 514 can include databases of reference imagery and/or other reference data, which may be used in image analysis. Remote data 514 can also include a repository of captured images and/or other sensor data, such as from across time periods and/or from a plurality of drones.

Remote processing modules 516 may include flight control modules, e.g., for controlling navigation routes or destinations, image analysis modules, and/or action modules to determine actions to take. The remote control computer system 510 may receive data from one or more drones, store such data, process such data, and/or generate and transmit machine-readable instructions to the drones.

As discussed above, in one embodiment, the device is an apparatus having image capturing capabilities and image recognition capabilities coupled with software that is programmed to determine whether or not an object in an image field is a pistil. A "pistil" herein is any physical, identifiable structure or shape of a plant part that is adapted to receive pollen. Once a pistil is detected, an automatic response in an action arm directs pollen to the identified pistil.

As also discussed above, the device set forth herein may be programmed to provide an active response to remove, mitigate and/or react to various biological conditions. For example, in some embodiments, the device may be programmed to detect a presence of skin conditions and send an alert or expel a marking material to a body site where a condition is identified. In an illustrative embodiment, the device is programmed to detect ticks embedded on user's skin by recognizing physical features consistent with ticks, such as appearance, color, size, shape etc.

The tick-detecting device may be disposed on a movable platform, for example, as set forth herein, and programmed to move across an external aspect of a person or of a limb. In other embodiments, the device is a handheld unit that is grasped and manipulated by a user.

When a tick, bite, or mark is identified, the device automatically responds by directing the action head to the location of the detected tick and releases a blast of degradable ink, paint or similar marking material to designate a need for careful inspection or removal as the case may be.

In some embodiments of the invention, the device is programmable to be tailored to identified users for more specific tick detection. In such embodiments, the device is initially deployed to image the entire skin surface of a given user. The device detects all images that contrast with normal skin tone, and stores each of the images in a database (e.g. on a digital storage medium). Thus, after initial deployment, the system's database will have images of each mole, scar, or other dark marks on the user's skin. Upon subsequent deployment, the system will search for contrasting images and compare each contrasting image detected against the stored database. If a match is found, then the system can determine that the detected image was previously present on the user and no action is necessary. If, however, an image is detected for which there is no match—the system will then direct the action head to mark the newly found image. In this embodiment, a tick will present as an image for which there is no corresponding match, and it will trigger a response of the action head as set forth above.

Still in other embodiments, the device set forth herein may be programmed to provide an active response to remove, mitigate and/or react to various agricultural conditions.

For example, the device may be deployed in a field, garden, or orchard to detect early indications of weeds or similar harmful plants. The device may be provided on a stationary structure to scan an area of a field. Alternatively, the device may be mounted on a movable platform such as a robot, vehicle, or drone that is utilized to travel about a field and obtain images of plants growing therein. The software is programmed to distinguish between a weed and a desired crop or plant. When it detects any of various features associated with weeds or other undesired vegetation it will automatically react. In one embodiment, the device is trained to detect weeds by recognizing physical features such as appearance, color, size, shape etc. In the event that weeds are detected, the device automatically responds by directing the action arm to the detected weed or plant and releasing herbicide to the vicinity of the detected weeds.

In another illustrative embodiment, the devices and systems described herein can be in the form of a security system used to identify and/or target other offending objects, such as drones and other mechanical devices which can move in the air, on the ground, or through the water. Such security systems can be used to keep an area secure and/or free from threats. For example, such a security system can be used by a prison to prevent drones from flying over prison grounds and delivering contraband to prisoners. Such a security system can also be used to help protect military bases, bunkers, supply caches, communication towers, homes, etc. from spying and/or attacks implemented using mechanical devices.

In one embodiment, a security system can include a mobile platform that allows the system to traverse land, air, and/or water. For example, the system can include tracks that allow the mobile platform to move along the ground, propellers or other thrust component to allow the mobile platform to move through the air, and/or lightweight inflatable pontoons using in conjunction with a thrust component that allows the mobile platform to float and move through the water. The system can also include one or more image capture devices, one or more processors, one or more computer memories, one or more communication components for communicating with remote systems, control and logic software, and/or one or more detectors such as motion detectors, sound detectors, wireless signal detectors, one or more action arms, etc. mounted to the mobile platform.

The one or more image capture devices for the security system can include still cameras, video cameras, infrared imaging devices, x-ray imaging devices, magnification lenses, etc. that are configured to capture images of a given area. Captured images/data can be stored in a computer memory of the security system and/or transmitted to a remote storage/processing system using the communication components. The computer memory of the security system can also be used to store the control and logic software, which can be used to identify objects and make determinations regarding what, if any, action is to be taken upon identification of an object. The logic can include image recognition software that can be used to analyze images/video captured by the system to determine if any offending objects are present. The control and logic software can be executed by the one or more processors of the system. In an illustrative embodiment, the security system can be configured to determine whether an identified object is a living object (i.e., person, bird, animal, etc.) or an inanimate object (drone, robot, etc.). The action taken by the system can be based in part on whether the object is living or inanimate.

The one or more sensors of the security system are used to detect the presence of objects and to help determine whether detected objects are considered offending objects. A motion detector sensor can be used to identify motion, which can be indicative of an approaching object. A microphone or other noise detector can be used to detect sounds which can be indicative of an approaching object, such as motor noise, propeller noise, electronics noise, voices, etc. A wireless signal detector can be used to detect approaching objects based on wireless signal transmissions made by the approaching object. The security system can also include a temperature probe detector for determining the temperature at or near an approaching object. The security system can also include an infrared detector to detect whether an approaching object is releasing any heat.

Figure 6:
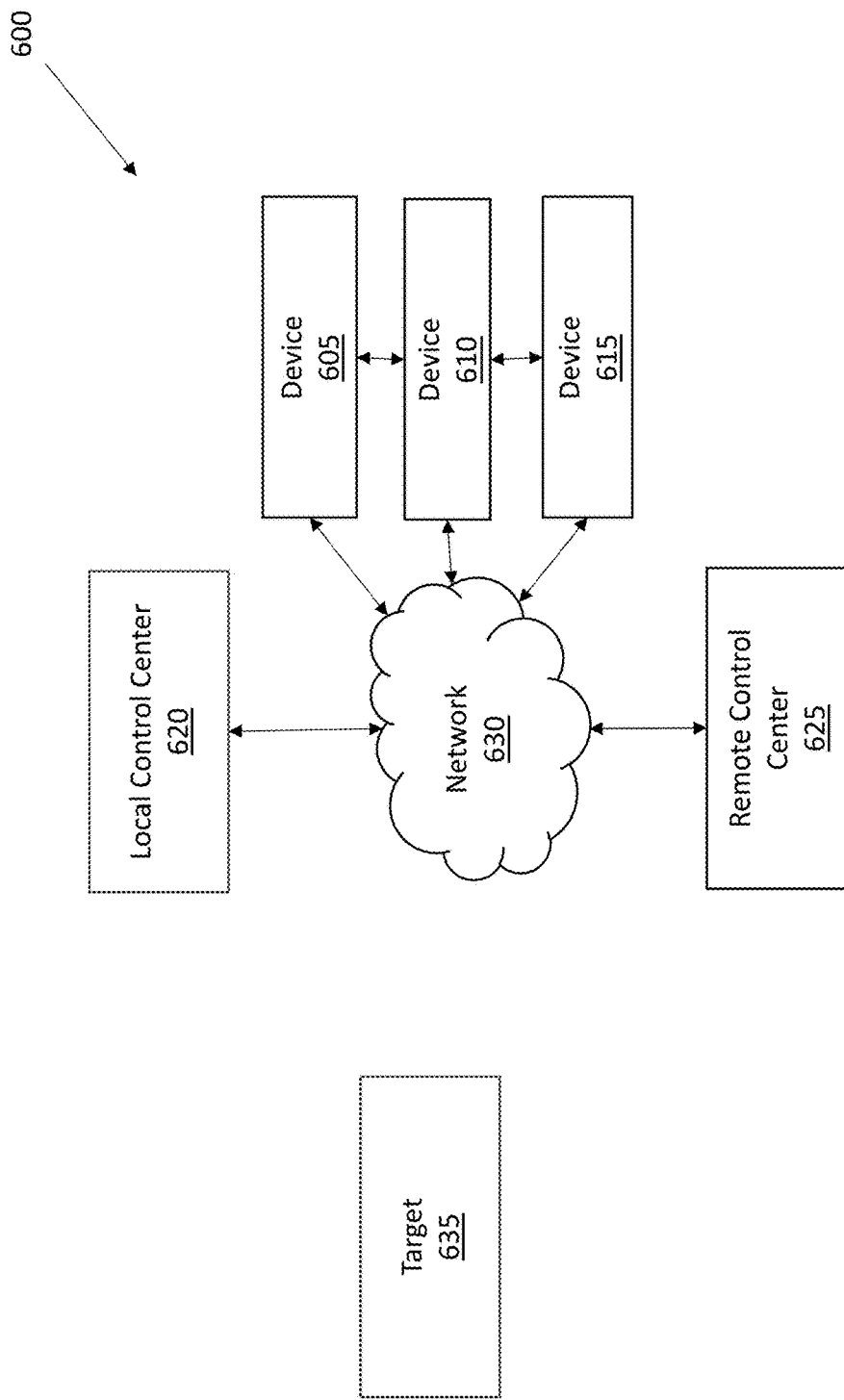
FIG. 6 is a block diagram depicting a system to target mechanical offending objects in accordance with an illustrative embodiment.

FIG. 6 is a block diagram depicting a system 600 to target mechanical offending objects in accordance with an illustrative embodiment. As depicted, the system 600 includes a device 605, a device 610, a device 615, a local control center 620, a remote control center 625, and a network 630. In alternative embodiments, the system 600 can include fewer, additional, and/or different components. In an illustrative embodiment, each of the devices 605, 610, and 615 can be mechanical devices which are configured to monitor an area and take action based on the monitoring. The area being monitored can be a school, a prison, a government building, a home, a business, a warehouse, a military base, etc.

In an illustrative embodiment, each of the devices 605, 610, and 615 can include a mobile platform, an image capture device, one or more sensors, a processor, a memory, a transceiver, a power source, and an action arm. The mobile platform can allow the devices 605, 610, and 615 to fly through the air, to move along the ground, and/or to float and move on water. As such, each of the devices 605, 610, and 615 can be in the form of a drone, watercraft, wheeled vehicle, robot, etc. The one or more sensors on the devices can include motion detector sensors, microphones, temperature sensors, wireless signal sensors, infrared sensors, etc. As discussed above, these sensors can be used to detect the presence of an object and/or to determine whether a detected object is living or inanimate.

The memory of the devices 605, 610, and 615 can be used to store algorithms and operating logic, and the processor can execute the algorithms and logic. The transceiver, which can be controlled by the processor, allows the devices 605, 610, and 615 to communicate with one another, either directly or through a network 630. The transceiver also allows the devices 605, 610, and 615 to communication with the local control center 620 and the remote control center 625. The network 630 can be any type of network known in the art, such as a cellular network, a short-range communication network, a radio frequency network, the Internet, etc.

The local control center 620 can be proximate to the area being monitored, and can include docking stations or other components to periodically charge the power sources of the devices 605, 610, and 615. The power sources can be in the form of batteries or any other charge generating/storing devices. The local control center 620 can also include at least a processor, memory, and transceiver. The local control center 620 can be configured to receive images/video captured by the image capture device and data detected by the sensors, and can process that received data to determine whether a possible target, such as a target 635, is present. In the event of a possible target, the local control center 620 can generate instructions for one or more of the devices 605, 610, and 615 to take action. In an alternative embodiment, each of the devices 605 may perform data processing on-board and may make independent decisions regarding any action to be taken.

In another embodiment, any of the processing and/or decision-making can be performed by the remote control center 625. The remote control center 625 can be located in a remote position relative to the area being monitored by the system. As one example, the remote control center 625 can be a hub/facility which is tasked with the monitoring of a plurality of different locations. In one embodiment, data processing and instruction generation can normally be performed at the local control center 620 or on-board the devices 605, 610, and 615, but can be overridden by the remote control center 625 for sensitive or particularly important scenarios. In an alternative embodiment, the remote control center 625 may not be included.

In an illustrative embodiment, one or more of the devices 605, 610, and 615 can identify the target 635 using its image capture device and/or other sensors. The target 635 can be a drone or other mechanical device, a person, or an animal. Upon detection of an object, the system determines what, if any, action is to be performed by the devices 605, 610, and 610. In one embodiment, the system 600 determines whether the target 635 is living or inanimate and bases the action determination on the result. For example, if the target 635 is determined to be living, the system 600 may perform one or more notification operations to alert appropriate individuals of a person or other living thing the area that is being monitored. If the target 635 is determined to be inanimate, the system 600 can instruct one or more of the devices 605, 610, and 615 to take action using their action arms.

In one embodiment, if a determination is made by the system 600 to take action, one or more of the devices 605, 610, and 615 is instructed to use their action arms to capture or disable the target 635. The target 635 can be captured by a net that is launched from an action arm of one of the devices, and that is configured to inhibit further movement of the target 635. The action arm can also be used to fire a projectile at the target 635 to disable it. The projectile can be a bullet, a rubber bullet, a bean bag, a paint ball, an arrow, or any other type of projectile. In one embodiment, the action arm can include a flamethrower that is configured to direct fire toward the target 635. The action arm can also include a laser that is configured to direct a laser beam at the target 635 to disable or destroy it. The action arm can further include a signal jammer or interference unit that is designed to disable wireless communications from being transmitted or received by the target 635.

In another illustrative embodiment, any of the systems described herein can be used for detection of explosive devices such as landmines, bombs, artillery, etc. Thousands of individuals die every year as a result of unintentional detonation of explosive devices such as abandoned landmines. A landmine refers to a type of explosive device that is positioned on the ground or just under the surface of the ground as part of a military operation. The landmine is designed to explode when contacted or approached by an individual or vehicle. Thousands of landmines may be placed during a military conflict. Unfortunately, the landmines are often not removed at the conclusion of the conflict, which creates a very dangerous environment for animals and individuals living in the area. Other unexploded munitions such as bombs, artillery shells, missiles, etc. can also cause hazardous conditions.

Described herein is a system that is configured to detect and act upon undetonated explosives. In one embodiment, the system can use the principle of induction heating to identify explosives above, at, and below ground level. The system can also be configured to use gas sensing to identify the explosive devices. Specifically, one or more gas sensors are used to identify the presence of gases which are released over time as certain types of explosive devices degrade. The system is also configured to take an action with respect to the identified explosive such as cause detonation, mark the location, transmit data regarding the location, etc.

Figure 7:
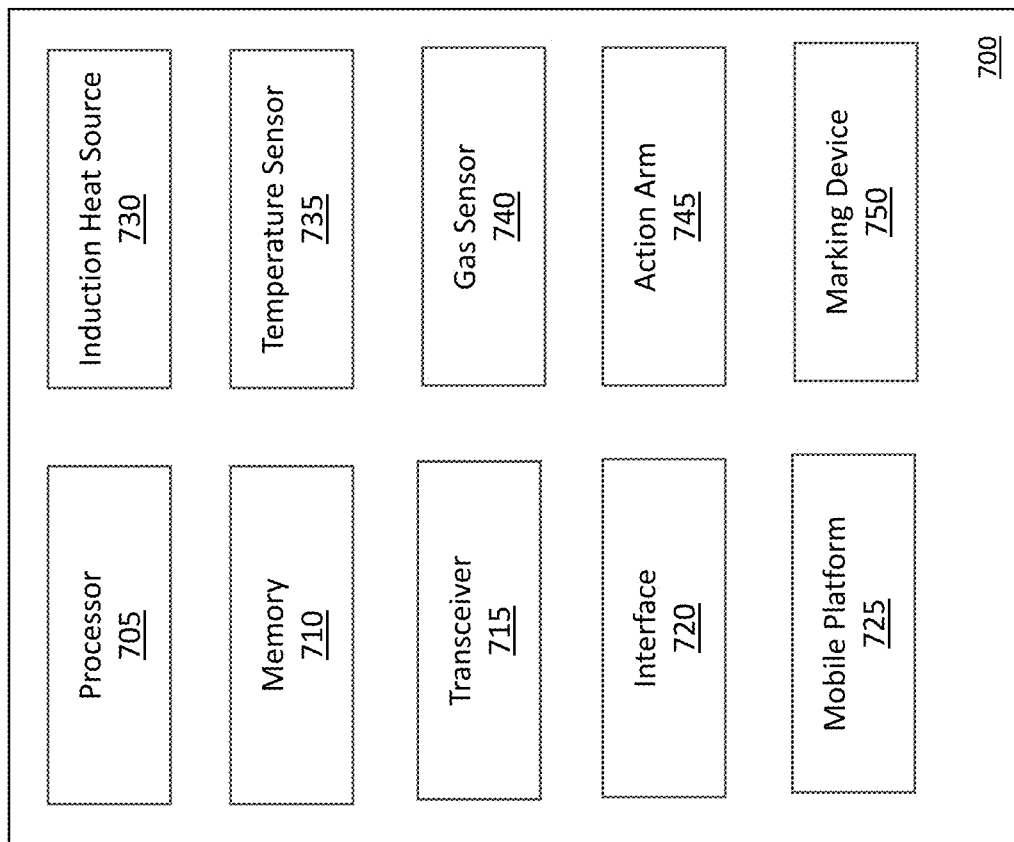
FIG. 7 is a block diagram of a system to target undetonated explosive devices in accordance with an illustrative embodiment.

FIG. 7 is a block diagram of a system 700 to target undetonated explosive devices in accordance with an illustrative embodiment. The system 700 includes a processor 705, a memory 710, a transceiver 715, an interface 720, a mobile platform 725, an induction heat source 730, a temperature sensor 735, a gas sensor 740, an action arm 745, and a marking device 750. In alternative embodiments, the system 700 may include additional, fewer, and/or different components. For example, the system 700 may include a power source, a protective housing, a camera, and/or any of the other functionality and hardware described herein for the various systems.

The processor 705 of the system 700 can be any type of computer processor or controller known in the art. Similarly, the memory 710 can be any type of computer memory or storage known in the art. The memory 710 can be used to store operating instructions for the system 700, algorithms for identifying explosive devices, algorithms for taking action with respect to identified explosive devices, communication algorithms, navigation algorithms, etc. The processor 705 can be in communication with the memory 710 and configured to execute any of the operating instructions and algorithms stored in the memory. The processor 705 can also be used to interact with and control any of the other components of the system 700.

The transceiver 715 can be any type of transmitter and/or receiver known in the art. The transceiver 715 allows the system 700 to communicate with a remote location such as a docking station, a control station, a handheld remote control unit, cellular towers, satellites, etc. The transceiver 715 allows the system 700 to receive remote instructions and/or to provide captured data to a remote location. For example, as discussed in more detail below, the system 700 can be used to identify an explosive device that has not detonated. In one embodiment, upon identification of the explosive device, the system 700 can use the transceiver 715 to transmit an image and/or other data regarding the identified explosive device such that a remote user can instruct the system 700 with an appropriate course of action. In an alternative embodiment, the system 700 can include instructions in the memory 710 that instruct the system 700 on how to respond to one or more types of different identified explosives.

The interface 720 can include any components that allow a user to interact with the system 700. The interface 720 can include a display, a keyboard or keypad, one or more ports, etc. The user can utilize the interface 720 to exchange information with the system 700, to program the system 700, to conduct diagnostics on the system, etc. In an alternative embodiment, the interface 720 may not be included in the system 700.

The mobile platform 725 can include one or more housings used to mount the components of the system 700. The mobile platform 725 also allows the system 700 to traverse land, air, and/or water. For example, the mobile platform 725 can include tracks and/or tires that allow the mobile platform to move along the ground. The mobile platform 725 can also include one more propellers, blades, or other thrust component to allow the mobile platform to move through the air. For example, the mobile platform 725 can include any air drone components known in the art. The mobile platform 725 can also include flotation and propulsion components that allow the system to float and move through water. The flotation components can include lightweight inflatable pontoons or other buoyant material, and the propulsion component can include a propeller or jet.

The induction heat source 730 of the system 700 can be used to generate detectable heat in a metal component that forms an explosive device (e.g., a housing of the explosive). The induction heat source 730 can include an electromagnet and an electromagnetic radiation source that can be in the form of an electronic oscillator that passes a high frequency alternating current through the electromagnet. Alternatively, the induction heat source 730 can include any other electromagnetic radiation source that can be used to induce heat in a metallic object. The radiation emitted by the induction heat source 730 can be targeted such that it causes eddy currents to form in a metallic object such as an explosive housing, which in turn causes the metallic object to heat up. If the metallic object is ferromagnetic, heat may also be induced via magnetic hysteresis losses as known in the art.

The temperature sensor 735 can be any type of temperature probe, thermometer, thermocouple, etc. known in the art for detecting heat. In an illustrative embodiment, the temperature sensor 735 is used to detect a metallic object by detecting heat that emanates from the metallic object as a result of exposure to radiation from the induction heat source 730. In one embodiment, the temperature sensor 735 can be on a movable arm or other component that allows for precise positioning of the temperature sensor 735 such that the temperature sensor 735 can be placed into an area of interest (e.g., near the ground or in the ground) to detect heat. Upon detection of heat, the system 700 can determine that there is a potential explosive in the area. In an illustrative embodiment, the temperature sensor 735 detects the heat as a differential between ambient environment conditions and the heat emitted from the metallic object as a result of the induction heating.

The gas sensor 740 can be used to detect one or more gasses that are commonly emitted from an explosive over time. For example, it is known that many explosive devices emit detectable chemical vapor(s) such as nitrogen dioxide, 2,4,6 trinitrotoluene, 2,4 dinitrotoluene, 1, 3 dinitrobenzene, etc. As with the temperature sensor 735, the gas sensor 740 can also be on a movable arm or other component that allows for precise positioning of the gas sensor 740 relative to a surface of interest such as the ground or under the ground. In one embodiment, the gas sensor 740 can be used independent of the induction heat source 730 to detect explosive devices that do not contain metal and which therefore cannot be heated via induction (i.e., plastic explosives). In an alternative embodiment, the gas sensor 740 can be used in conjunction with the induction heat source 730. For example, upon detection of a metallic object using the induction heat source 730 and the temperature sensor 735, the gas sensor 740 can be used to determine if any gas(es) indicative of an explosive device are present in the area to improve the likelihood that the identified metal is actually an explosive device.

In one embodiment, upon detection of a possible explosive device, the system 700 can be configured to take action to attempt to detonate the explosive device. The action arm 745 can include one or more components that can be used to perform the detonation. In one embodiment, the action arm 745 can include a contact surface that is configured to physically contact the explosive (e.g., landmine) to cause detonation in the same way that individual walking over the explosive would cause it to detonate. The action arm 745 can also include components to generate a high thrust blast of air (or other gas) to cause the detonation without physically contacting the explosive. In one embodiment, the action arm 745 can include a compressed gas canister (e.g. carbon dioxide) to generate the high thrust blast. The action arm 745 can also include a gun, slingshot, pressurized launcher, or other component configured to shoot a projectile at the explosive to cause detonation. In an alternative embodiment, the system 700 can use the induction heat source 730 to generate a large amount of heat at the explosive device to cause the detonation.

The marking device 750 can be used to mark the location of a possible explosive device. The marking device 750 can include a paint source to apply a paint to the ground where the explosive may be located. The marking device 750 can also determine, save, and/or transmit coordinates of the possible explosive using a highly accurate electronic positioning system incorporated into the system 700. For example, coordinates can be determined using temporary and/or permanent base stations and triangulation as known in the art. A high accuracy global positioning system (GPS) can also be used alone or in combination with a dead reckoning system to achieve coordinates with accuracy down to the range of inches. Any other electronic positioning system known in the art can also be used.

In one embodiment, the marking device 750 can be used in the event that a possible explosive is found but unable to be detonated by the system 700 after one or more detonation attempts. Alternatively, the marking device 750 can be used to mark any location at which a possible explosive is identified, regardless of whether a detonation attempt is made. In one embodiment, the system 700 can be programmed to make a determination of whether to use the marking device 750 to mark the location of a possible explosive device or the action arm 745 to attempt to detonate the possible explosive device. The determination can be based on the specific location at which the possible explosive device is located (e.g., extra caution may be used in an area close to homes, roads, etc.).

As an example, the system 700 can be used to survey an area to identify and/or dispose of any undetonated explosives. The area can be a prior military zone in which it is known or suspected that landmines and/or other explosives are present. The system 700 can use the mobile platform 725 to either fly over the area or drive over the area to perform detection tests. In one embodiment, the system 700 can use the transceiver 715 to communicate with a remote control station (or remote control unit) to provide information as it is detected and receive instructions responsive to the provided information. The instructions can include performing a detonation attempt, marking a location, and/or conducting additional detection testing of the location to help confirm what is present.

As the system 700 moves over the area, the system can utilize the induction heat source 730 to emit electromagnetic radiation that will induce heat in metallic objects that are proximate to the radiation. The metallic objects can be at, above, or below the ground surface. The temperature sensor 735 can be used in conjunction with the induction heat source 730 to detect heat from the metallic object(s), which is indicative of the presence of metal. In one embodiment, a temperature threshold (e.g., 1 degree above ambient conditions, 3 degrees above ambient conditions, 5 degrees above ambient conditions, etc.) can be used to reduce false positives caused by small pieces of metal and/or minerals. For example, if the detected temperature is less than the temperature threshold, the system 700 can determine that the identified metal is not part of an explosive. In an illustrative embodiment, the temperature sensor 735 is positioned on an arm or other movable component that allows precise positioning of the temperature sensor at a location which is being targeted with radiation by the induction heat source 730. The arm or other movable component also allows the temperature sensor 735 to positioned away from the system 700 such that heat generated by the system 700 does not interfere with the temperature sensor 735.

In one embodiment, upon detection of heat that satisfies the temperature threshold, the system 700 can attempt to detonate an explosive associated with the detected metal. In such an embodiment, the action arm 745 is activated to perform detonation. If the detonation is successful, the system 700 may be sacrificed. However, the cost of replacing the system 700 is negligible compared to the potential loss of human/animal life that could have otherwise resulted had the explosive detonated in response to human/animal contact. In an alternative embodiment or in situations where the detonation attempt fails, the system 700 can use the marking device 750 to mark the location for future action.

In one embodiment, the system can also use the gas sensor 740 to help detect possible explosives. The gas sensor 740 can be used to help confirm that detected metal (i.e., metal detected using the induction heat source 730) is actually associated with an explosive device based on the presence or absence of one or more signature gases associated with the decay of an explosive. Alternatively, the gas sensor 740 can be used independent of the induction heat source 730 and temperature sensor 735 to detect explosives based solely on the presence of the aforementioned gas(es). The action arm 745 can be used to attempt to detonate any explosives used by the gas sensor 740. The marking device 750 can also be used to mark the location in addition to or alternative to the detonation attempt.

The systems described herein can also be used in detector applications, such as portable or stationary metal detectors for use in monitoring individuals and crowds in a given area. In one embodiment, a stationary induction detector system can be positioned on a street, at an entrance to a facility/event, in a mall, etc. and used to determine whether individuals entering a store, park, concert, hotel, tourist attraction, secure area, airport, etc. are carrying metal. The induction detector system can be implemented as a walkway through which individuals are required to pass prior to gaining entry, similar to metal detection systems used in airports and other buildings. In one implementation, the induction detector system generates electromagnetic radiation that causes an increase in temperature of ferromagnetic metals that are positioned proximate to the induction detector system. Thermal sensors are positioned within the detection system and are used to trigger an alarm or take other action if metal is determined to be present. In an illustrative embodiment, the electromagnetic radiation is controlled such that the increase in temperature of the ferromagnetic metals is minimal and does not cause pain or discomfort to individuals carrying the ferromagnetic materials. For example, the temperature increase may be controlled to be between 0.1 and 5 degrees Fahrenheit. Alternatively, other values of temperature increase may be used, such as between 1 and 7 degrees Fahrenheit, between 0.5 and 10 degrees Fahrenheit, etc.

In another implementation, an induction detector system can be a portable device in the form of a handheld unit such as a wand, etc. The handheld induction detector system can be used by security guards to scan individuals entering a facility/event. Specifically, the handheld induction detector system can generate electromagnetic radiation and use one or more on-board temperature sensors to detect an increase of temperature in present metals that results from the electromagnetic radiation. The portable device can also be used in military operations to identify metallic objects behind walls of buildings or within the walls of buildings. The portable device can also be used by construction crews to identify metal within a wall. For example, the portable device can be used to detect the location of water pipes within walls, electrical wiring within walls, bombs behind walls, firearms behind walls, etc.

Figure 8:
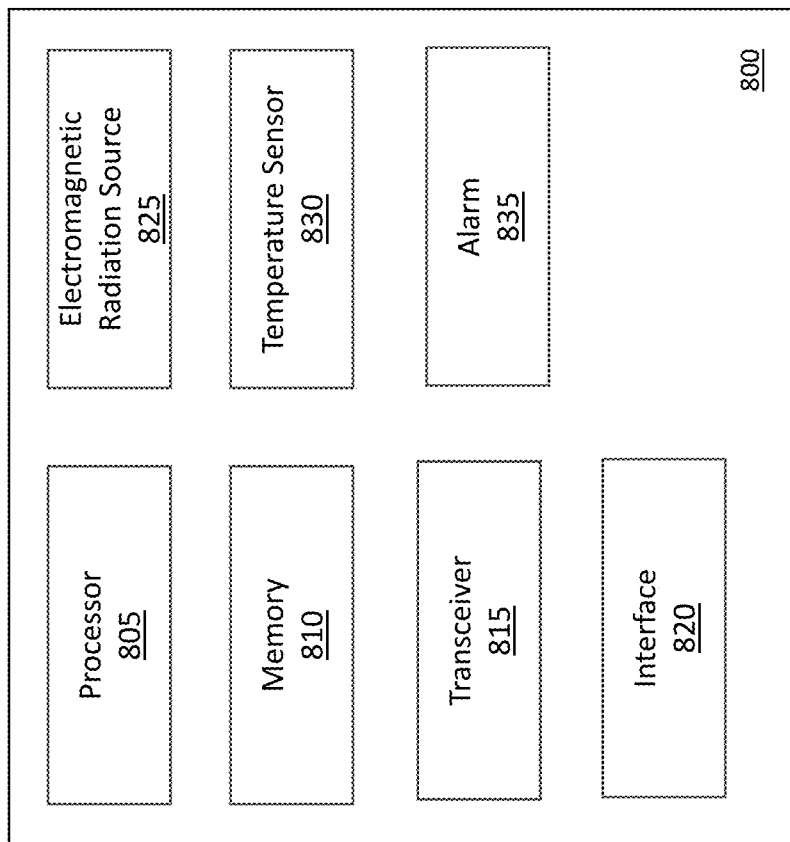
FIG. 8 is a block diagram of an induction detector system in accordance with an illustrative embodiment.

FIG. 8 is a block diagram of an induction detector system 800 in accordance with an illustrative embodiment. The induction detector system includes a processor 805, a memory 810, a transceiver 815, an interface 820, an electromagnetic radiation source 825, a temperature sensor 830, and an alarm 835. In alternative embodiments, the induction detector system 800 may include fewer, additional, and/or different components. As discussed above, the induction detector system can be implemented as a stationary unit or a portable unit, depending on the application.

The electromagnetic radiation source 825 can be any type of electromagnetic radiation generating system known in the art. In the embodiment of a stationary induction detector system, the electromagnetic radiation source 825 directs the electromagnetic radiation to a detection area inside of a gate, tunnel, arch, chamber, etc. in or on which the components of the induction detector system 800 are mounted. For example, individuals being tested by the detection system can be directed to stand on a certain spot/location which forms the detection area. Alternatively, the detection area may be a larger area such as a street, sidewalk, entryway, etc. that is monitored without asking the user to stand on a certain spot/location. As a result of the electromagnetic radiation, any ferromagnetic metal within the detection area heats up. The temperature sensor 830 is used to detect the resulting heat caused by the interaction of the metal and the electromagnetic radiation. The temperature sensor 830 can be any of type of temperature/thermal sensor known in the art such as an infrared heat detection unit, and can include a plurality of sensors positioned within or around the detection area of the system. In at least one embodiment, the sensors may be mounted on a handheld wand or a movable platform that moves around the individual being scanned.

Upon detection of a temperature increase of an individual within the detection area, the alarm 835 can be triggered to indicate the presence of metal. Alternatively, an alarm may not be triggered so that offending individuals are not aware that they have been detected. The alarm, if used, can be an audio alarm, a visual alarm, an audiovisual alarm, a tactile alarm, etc. The alarm 835 alerts an operator of the detection system to the presence of metal so that a search of the individual or other action can be taken prior to allowing the individual to enter the event/building. In one embodiment, the system uses a temperature increase threshold to determine whether to trigger the alarm 835. The temperature increase threshold can be relative to an ambient environmental temperature and/or relative to a body temperature (i.e., 98.6 degrees Fahrenheit (F)) of the individual being tested. For example, on a day when the ambient temperature is 70 degrees F., it would be expected that no part of an individual being tested should exceed his/her body temperature, and the temperature threshold for triggering the alarm 835 can be 100 degrees F., 102 degrees F., 105 degrees F., etc. On a day when the ambient temperature is 110 degrees F., it would be expected that no part of the individual being tested should exceed 110 degrees F., and the temperature threshold for triggering the alarm 835 can be 112 degrees F., 115 degrees F., etc.

In an embodiment in which the temperature threshold is based at least in part on ambient environmental temperature, the temperature threshold is dynamic such that it changes as the ambient temperature changes. For example, the temperature threshold can be set to a predetermined number of degrees greater than the ambient temperature, where the predetermined number of degrees can be 1 degree, 2 degrees, 5 degrees, 10 degrees, etc. In one embodiment, the system is configured to determine the temperature threshold based on the greater of the individual's body temperature and the ambient environmental temperature.

The processor 805 is used to control the induction detector system 800, and can be any type of computer processor or controller known in the art. For example, the processor can be used to run an algorithm to dynamically determine a temperature threshold for triggering the alarm 835 based on ambient temperature of the environment in which the detection system is located. The processor 805 can also compare a temperature detected by the temperature sensor 830 to the temperature threshold and trigger the alarm 835 if the temperature threshold is exceeded. The processor 805 can also be used to calibrate the temperature sensor 830, to control and interact with the memory 810, to control and interact with the transceiver 815, and to control and interact with the interface 820.

The memory 810 can be any type of computer memory or storage known in the art. The memory 810 can be used to store system information such as a temperature threshold, an algorithm for dynamically adjusting the temperature threshold, an algorithm for determining whether to activate the alarm 835, an operating system, a log of detected data, etc. The algorithms can be stored as computer-readable instructions on the memory 810, and the memory 810 can be a non-transitory computer-readable medium that is accessible by the processor 805.

The transceiver 815 can be any type of receiving and/or transmitting device known in the art. The transceiver 815 can be used to transmit an alert to a remote location upon detection of metal by the system. The transceiver 815 can also be used to receive programming instructions, temperature threshold data, algorithms, etc. from a remote location through a network such as the Internet. The interface 820 includes one or more components that allow an operator to interact with the system 800. For example, the interface 820 can include a display, a mouse, a keyboard, ports, a microphone, a speaker, switches or other manual system controls, etc. The interface 820 allows the operator to control the system, program the system, reset the system, perform troubleshooting on the system, etc.

In one embodiment, the induction detector system also includes one or more cameras. The one or more cameras can be used to capture one or more images of all individuals who are tested by the system. Alternatively, the one or more cameras can be used to capture one or more images only of the individuals that trigger the alarm 835. The captured images can be stored in the memory 810, presented on the interface 820, and/or sent to a remote location using the transceiver 815.

As one example implementation, the induction detection system is implemented as a stationary system that includes a detection system for monitoring an area. The detection system can include a housing in the form of a gate, arch, tunnel, chamber, wall, etc. that a user enters, walks through, or walks past prior to entering a building, event, or other monitored area such as a street or sidewalk. In one embodiment, the detection system is partially or entirely surrounded by an electromagnetic radiation shield to ensure that any generated radiation remains in the detection area of the system and does not contact or affect bystanders that are proximate to the system.

In one implementation, individuals are monitored as they walk past or through a given area, and the individuals may or may not be aware of the presence of the induction detection system. In another embodiment, the user can be asked to remove all metallic objects from his/her person prior to entering or passing the housing of the induction detector system, similar to the process of going through a metal detector at an airport. The detection system can also be accompanied by warnings to warn individuals of possible health issues that can occur due to metallic implants. In one embodiment, the user is asked to stand still at a specific location (i.e., a detection area) within the housing while the individual is tested for metal. In one implementation, one or more walls of the housing surround the user and have temperature sensors incorporated therein to detect any generated heat. The one or more walls can be stationary or they may move relative to the individual to perform detection on all areas of the individual. Alternatively, instead of walls, one or more arms or other projections can be mounted on a movable platform and used to scan the individual's entire body for generated heat that results from the introduction of the electromagnetic radiation into the detection area.

Detected temperatures resulting from the scanning of the individual's body are compared to a temperature threshold, which can be set as an outright temperature (such as X degrees), a temperature range, or as a temperature change relative to the individual's body temperature or the ambient environmental temperature. For example, if set as an outright temperature, the temperature threshold hold may be 90 degrees, 100 degrees, 105 degrees, etc. If the temperature threshold is set as a temperature relative to body temperature or ambient temperature, the threshold may be 1 degree, 2 degrees, 5 degrees, 10 degrees, 25 degrees, etc. If the temperature threshold is exceeded, the alarm is triggered. As a result of the alarm, the individual may be searched and/or refused entry to the building or event.

In one embodiment, the detection system is configured to monitor a plurality of individuals simultaneously using an array of heat sensors that may be spread out over the detection area. As used herein, the array of heat sensors refers to one or more heat sensors. The plurality of individuals can be part of a crowd that is entering a venue, walking down a sidewalk, walking in a mall or store, etc. One or more electromagnetic radiation sources are used to target the plurality of individuals, causing any metal on their person to heat up slightly as described herein. One or more thermal sensors is used to monitor each of the plurality of individuals to detect any change in temperature that occurs as a result of induction heating due to the electromagnetic radiation. In one embodiment, the computing system of the detector includes artificial intelligence (e.g., algorithms) that individually monitors the plurality of individuals and keeps track of the temperature change for each of the individuals.

As an example, the system may simultaneously monitor 10 individuals that walk past the detection system on a sidewalk. The system can associate one or more thermal sensors with each of the 10 individuals to independently determine any temperature increase associated with each individual as a result of the radiation. In one embodiment, the temperature sensors obtain an initial temperature of each individual prior to radiation exposure, and then one or more secondary temperatures of each individual after the radiation exposure. The initial and secondary temperatures can be obtained by the same sensors/detectors, or different arrays can be used to obtain the initial and secondary temperatures. If the difference between the initial temperature and one or more secondary temperatures of the individual exceeds a threshold, an alert can be triggered. The system can also capture one or more images of each of the individuals and associate the one or more images with a detected temperature increase for that individual. In the event that the detected temperature increase (or lack thereof) triggers an alert, security personnel can use the one or more images to help ensure that they approach the correct individual for a search or questioning. In alternative embodiments, other numbers of individuals in a crowd may be monitored simultaneously by the system, such as 1, 2, 5, 15, 25, 100, etc.

In an illustrative embodiment, the artificial intelligence of the detection system can use machine learning to identify detection patterns that help determine what the temperature thresholds are for the system. For example, the system may determine that a vast majority of individuals (e.g., 95% or more, 98% or more, 99% or more, 99.9% or more, etc.) carry an amount of metal which results in a given range of temperature increases in response to the radiation. This normal temperature increase range can be, for example, between 0.5 degrees and 3 degrees. Alternatively, other temperature increase ranges may be found such as between 0.2 degrees and 1 degree, between 0.5 and 2 degrees, between 1 degree and 6 degrees, etc. Individuals who are considered to have a normal temperature increase do not trigger a system alert. However, individuals with a temperature increase that falls below or above the normal temperature increase range can trigger the system alert. An individual who triggers a temperature increase above the normal temperature increase range may be carrying an unusual amount of metal, which warrants further investigation to determine if the individual is carrying a weapon or other dangerous/prohibited item. An individual who triggers a temperature increase below the normal temperature increase range may be intentionally carrying little or no metal in an effort to avoid detection, which warrants further investigation to determine whether the individual may be carrying a plastic weapon or other unauthorized device.

An example system for monitoring an area includes a processor and an electromagnetic radiation source in communication with the processor. The electromagnetic radiation source is configured to emit radiation to heat a metallic object that is in or carried by a target. The system also includes an array of temperature sensors in communication with the processor, where the array of temperature sensors is configured to detect a first temperature associated with the target and a second temperature associated with the target. The first temperature is detected prior to emission of the radiation and the second temperature is detected subsequent to emission of the radiation. The processor is also configured to determine whether to trigger an alert based at least in part on a difference between the first temperature and the second temperature.

Continuing the example, the target can be a parcel, a piece of luggage, or a person in one embodiment. Additionally, the array of temperature sensors can be configured to simultaneously determine temperatures associated with a plurality of people. In one embodiment, the processor is configured to determine whether the difference between the first temperature and the second temperature falls within a normal temperature range, and the processor triggers the alert responsive to a determination that the difference between the first temperature and the second temperature falls above the normal temperature range. The processor may also trigger the alert responsive to a determination that the difference between the first temperature and the second temperature falls below the normal temperature range. The processor is also configured to automatically determine the normal temperature range based on a pattern that results from monitoring a plurality of targets.

Continuing the example, the system also includes an image capture device to capture an image of the target, and the processor is configured to associate the image with the target such that the first temperature and the second temperature are also associated with the target. The processor also associates the image of the target with the alert. The system can also include one or more housings to house at least the array of temperature sensors. The array of temperature sensors can include a first array of temperature sensors configured to detect the first temperature of a plurality of targets and a second array of temperature sensors configured to detect the second temperature of the plurality of targets.

An example method of monitoring an area includes emitting, from an electromagnetic radiation source, radiation to heat a metallic object that is in or carried by a target. The method also includes detecting, by an array of temperature sensors, a first temperature associated with the target and a second temperature associated with the target, where the first temperature is detected prior to emission of the radiation and the second temperature is detected subsequent to emission of the radiation. The method further includes determining, by a processor in communication with the electromagnetic radiation source and the array of temperature sensors, whether to trigger an alert based at least in part on a difference between the first temperature and the second temperature.

The example method also includes determining, by the processor, that the difference between the first temperature and the second temperature falls outside of a normal temperature range, and triggering the alert responsive to the determination that the difference between the first temperature and the second temperature falls outside of the normal temperature range. The method also includes determining, by the processor, the normal temperature range based on a pattern that results from monitoring a plurality of targets. In some embodiments the array of temperature sensors comprises a first array of temperature sensors and a second array of temperature sensors. The method includes detecting, by the first array of temperature sensors, the first temperature of a plurality of targets, and detecting, by the second array of temperature sensors, the second temperature of the plurality of targets. In some embodiments, the method also includes capturing, by an image capturing device, an image of the target, and associating, by the processor, the image with the target.

As another example implementation, the induction detector system 800 of FIG. 8 can also be formed as a portable detection unit that can be used to detect metal on an individual's person, metal in luggage or other purses, metal behind or within a wall, etc. The portable induction detector system can include a battery to power the system, or the system can be powered through a wall outlet or other power source. The portable detection unit can be a handheld wand in one embodiment, which is used to scan an individual for metal prior to allowing the individual to enter a building or event. For example, the wand can use an electromagnetic source (e.g., the electromagnetic radiation source 825) to induce heat in metallic objects such as knives or guns carried by the individual being tested. One or more temperature sensors on the wand are used to detect the temperature on or near the individual and to compare the detected temperature to a temperature threshold as described herein. If the temperature threshold is exceeded, an alarm is triggered and the operator is made aware that the individual being tested is carrying metal. In alternative embodiments, form factors other than a wand can also be used to implement the portable system.

As discussed above, the portable induction detection system can also be used to determine whether there is metal within or behind a wall. For example, a construction crew can use the portable induction detection system to determine the location of metallic pipes and/or wires within a wall using the techniques described herein. The construction crew can use this information to access the pipes/wires with accuracy, thereby causing minimal damage to the wall. The construction crew can also use this information to avoid the pipes/wires within the wall so that leaks, electrical hazards, and other problems are avoided. In another embodiment, the portable induction detection system can be used in military or police operations within a building to detect bombs, guns, artillery shells, and other potentially hazardous material that are inside of a wall or adjacent to the wall. In such embodiments, the heat sensor(s) of the portable induction detection system can be positioned adjacent to the wall to detect heat generated within the wall or on the other side of the wall.

In one embodiment, the electromagnetic radiation source of the induction detection systems described herein is adjustable such that varying amounts of heat can be generated in metallic objects. For example, a lower magnitude of electromagnetic radiation can be used in a stationary/portable detection system that is used on individuals to prevent the individuals from being burned due to excessive generated heat. Similarly, in an induction detection system used to detect metallic objects within or behind a wall, the electromagnetic radiation may be increased to generate higher temperatures which can be detected at a further distance from the system. Additionally, in the case of a plastic gun with metallic ammunition that is positioned behind a wall, the increased electromagnetic radiation can be used to excessively heat the metallic ammunition and at least partially melt the plastic gun, rendering it unusable. Similarly, the increased heating of a metallic gun, bomb, etc. behind a wall may make the weapon more difficult to use without the user getting burned.

In another illustrative embodiment, the temperature sensor(s) of the induction detection system can be used to detect motion behind or within a wall. As an example, an array of temperature sensors can be positioned on or adjacent to the wall, and the processor of the system can use the detected temperatures from each of the sensors to determine if the generated heat is moving or if it remains stationary. For example, a first temperature sensor can detect an increased temperature at a first location at a first time, and a second temperature sensor can detect an increased temperature at a second location at a second time. If, at the second time, the heat detected by the first temperature sensor at the first location has dissipated, such dissipation can be indicative of movement of a metallic object from the first location to the second location. The movement can be indicative of a person being present on the other side of the wall, and is used to determine an appropriate course of action. If, at the second time, the heat detected by the first temperature sensor remains, this can be indicative of a large metal object through which the heat resulting from the electromagnetic radiation is spreading.

As discussed above, in an illustrative embodiment, the electromagnetic radiation intensity can be controlled such that excessive heating of metallic objects does not occur. Such excessive heating could potentially cause damage to individuals and/or their property. In an alternative implementation, a high intensity and/or high frequency radiation source can be used to intentionally cause excessive heating of nearby metallic objects. For example, in the context of a standoff, military operation, hostage situation, etc. it may be desirable to attempt to excessively heat the metallic objects associated with a perpetrator in an effort to physically harm them and/or render their weapons unusable. For example, a metallic bullet can be heated to cause melting of plastic portions of a firearm, rendering the firearm unable to be fired. Similarly, a knife/firearm can be heated such that the perpetrator is unable to handle the weapon.

In another embodiment, a frequency and/or intensity of the electromagnetic radiation source can be continually cycled to varying magnitudes (e.g., high/low/high/low). Such cycling can help to offset the effect of a radiation shield used to block radiation, such as a graphite opaque shield. Specifically, cycling the frequency and/or intensity increases the likelihood of using a radiation signal that is not able to be blocked by the shield.

As discussed above, the embodiments described herein can also be used to detect metallic objects in luggage and shipping packages. For example, in situations where ferromagnetic metals are not supposed to be present in luggage or parcels, the presently described embodiments can be used to detect any ferromagnetic metals and generate an alert responsive to the detection. Specifically, electromagnetic radiation can be directed at the luggage/parcels and a temperature sensor used to detect any increase in temperature that occurs via induction heating as a result of the directed radiation. An increase in temperature indicates the presence of a ferromagnetic metal, which results in an alert to a system operator, who can then perform additional inspection of the luggage/parcel. A similar process can be used to detect hidden cameras, phones, microphones, etc. that include ferromagnetic metal. Specifically, radiation can be directed at an individual that may be carrying such surveillance items, and the resulting induction heating of the surveillance items can indicate their presence and/or render them unusable.

Another embodiment is directed to an induction system for mold remediation. Mold within a dwelling or other structure can cause serious health issues such as nasal and sinus congestion, respiratory problems, throat irritation, eye irritation, allergic reaction, etc. Mold is often found in between walls and in other areas in which the mold is not readily visible. Traditional techniques to remediate the mold involve tearing down the wall, removing the mold and/or materials covered with mold, and rebuilding the wall. Such a process is time consuming, expensive, and inconvenient to a homeowner.

Described herein is a system and method that utilizes induction heating to kill the mold. In an illustrative embodiment, induction heating is used to heat the mold to a temperature of ~160° Fahrenheit (F) for approximately 30 minutes to destroy the mold. If the mold is on an exposed (i.e., accessible) surface, a ferromagnetic plate or other material with ferromagnetic particles can be positioned on the mold, and an electromagnetic radiation source can be activated to direct radiation toward the ferromagnetic material. The material becomes hot through induction and is maintained at a desired temperature for a predetermined amount of time to remediate the mold.

However, as noted above, mold often accumulates in between walls and in other difficult to access areas. In order to use induction heating to remediate the mold in such scenarios, ferromagnetic particles are positioned near the mold and heated. In one embodiment, an expandable foam or a spray insulation is impregnated with ferromagnetic particles. In such an implementation, a small hole can be placed on one side of a wall and the expandable foam or spray insulation can be placed in between the walls through the hole. The expandable foam or spray insulation will expand to fill the space between the walls such that it is in contact with the mold. The ferromagnetic particles can also be incorporated into fiberglass (or other) insulation that is installed between the walls. An electromagnetic radiation source is activated and the radiation is directed toward the ferromagnetic particles in between the walls. The ferromagnetic particles become hot through induction, and the radiation is controlled to maintain the particles at a desired temperature for a predetermined amount of time to remediate the mold.

In another embodiment, ferromagnetic particles are impregnated into a wall board such as a gypsum board, a cement board, etc. that is used to form the walls of a structure. As a result, in the event of mold, there is no need to drill a hole in the wall or tear down the wall to perform heat remediation. Rather, electromagnetic radiation is directed to the portion(s) of the wall where mold is suspected, and the wall is heated to and maintained at a desired temperature to perform the remediation.

In another embodiment, a ferromagnetic sheet is used to cover all or a portion of the rear side of a wall board (i.e., the side of the wall board that is not visible after installation thereof). In such an embodiment, the ferromagnetic sheet may include openings to reduce the amount of material used. The openings can be sized such that the entire wallboard is still able to be heated through induction heating of the sheet. In such an embodiment, only a portion of the rear side of the wall board is in contact with the ferromagnetic sheet, and the portion can be 40%, 50%, 60%, 80%, etc. Alternatively, instead of a ferromagnetic sheet, a ferromagnetic mesh (e.g., a screen) can be used to cover the rear side of the wall board. In another embodiment, the ferromagnetic sheet or mesh can be incorporated into an interior of the wall board such that the sheet/mesh is not visible. Such an implementation can improve the structural integrity of the wall board and better enable both sides of the wall board to be heated through induction such that mold remediation can readily be performed on either side of the wall through induction heating.

Figure 9:
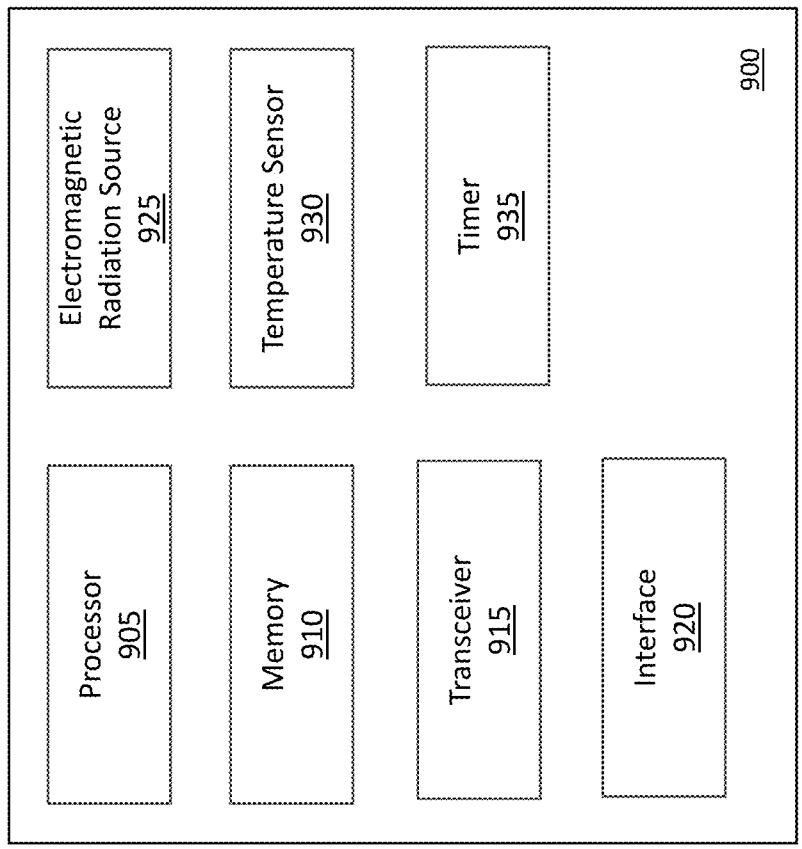
FIG. 9 is a block diagram of an induction system for mold remediation in accordance with an illustrative embodiment.

FIG. 9 is a block diagram of an induction system for mold remediation in accordance with an illustrative embodiment. The system 900 includes a processor 905, a memory 910, a transceiver 915, an interface 920, an electromagnetic radiation source 925, a temperature sensor 930, and a timer 935. In alternative embodiments, the induction system 900 may include fewer, additional, and/or different components. In an illustrative embodiment, the induction system can be implemented as a portable unit that can be moved into and throughout a building to perform mold remediation. The induction mold remediation system can also be implemented as a handheld unit that can be temporarily mounted to a wallboard to perform mold remediation.

The processor 905 is used to control the induction system for mold remediation 900. The processor 905 can be any type of computer processor or controller known in the art. The memory 910 can be any type of computer memory or storage known in the art. The memory 910 can be used to store system information such as a desired temperature at which to remediate mold, which can be ~140°, ~150°, ~160°, ~170°, etc. The memory 910 can also be used to store a time period for which the desired temperature is to be maintained to remediate the mold, such as 30 minutes, 1 hour, 2 hours, 3 hours, etc. The memory 910 can further be used to store one or more algorithms for controlling the electromagnetic radiation source 925 to reach and maintain the desired temperature. The algorithms can be stored as computer-readable instructions on the memory 910, and the memory 910 can be a non-transitory computer-readable medium that is accessible by the processor 905.

The transceiver 915 can be any type of receiving and/or transmitting device known in the art. The transceiver 915 can be used to transmit information to a remote device such as a smart phone, laptop computer, remote server, etc. The transmitted information can include data regarding the status of mold remediation, the maximum detected temperature at the mold remediation site, the duration of induction heating, the variation in temperature throughout the remediation process, etc. The transceiver 915 can also be used to receive programming instructions, desired temperature data, a time period or duration for which the remediation is to be performed, algorithms, etc. from a remote device through a network such as the Internet. The interface 920 includes one or more components that allow an operator to interact with the system 900. For example, the interface 920 can include a display, a mouse, a keyboard, ports, a microphone, a speaker, switches or other manual system controls, etc. The interface 920 allows the operator to control the system, program the system, reset the system, perform troubleshooting on the system, etc.

The electromagnetic radiation source 925 can be any type of electromagnetic radiation generating system known in the art. In an illustrative embodiment, the electromagnetic radiation source 925 is used to direct electromagnetic radiation at the ferromagnetic material (e.g., embedded particles, sheets, mesh, etc.) that is on or within a wall board. In another illustrative embodiment, the electromagnetic radiation source 925 is dynamically controlled to achieve and maintain the desired temperature for the desired duration of time. Dynamic control allows the system 900 to achieve and maintain the temperature in varying ambient conditions. For example, a greater amount of radiation may be used to maintain the desired temperature in a colder environment.

The temperature sensor 930 is used to detect the temperature of the wall board that results from the interaction of the ferromagnetic material and the electromagnetic radiation. The temperature sensor 930 can be any of type of temperature/thermal sensor known in the art, and can include a plurality of sensors positioned within or around the system 900. In at least one embodiment, the temperature sensor (or sensors) 930 is positioned on the side of the wall board upon which mold is being remediated. In one embodiment in which mold is between walls, the temperature sensor 930 can be placed between the walls through a small hole that is drilled into the wall. In an alternative embodiment in which no hole/opening is made in the wall, the temperature sensor 930 can be placed on the opposite side of the wall board from where the mold is being remediated (i.e., on the accessible side of the wall board). In such an embodiment, the system 900 is configured to mathematically determine the temperature on the inaccessible side of the wall board based on the temperature of the accessible side of the wall board. The mathematical determination is based at least in part on the heat conductivity property of the wall board, which is based on the type of material that makes up the wall board and the thickness of the wall board. The timer 935 can be any type of timer/clock known in the art, and is used to keep track of the duration of mold remediation to ensure that the wall board has been heated for an appropriate amount of time.

In an illustrative embodiment, the processor 905 is configured to execute a mold remediation algorithm that is stored in the memory 910. The mold remediation algorithm is used to dynamically control the electromagnetic radiation source 925 to achieve a desired temperature to remediate the mold. As discussed, the amount of electromagnetic radiation used to achieve the desired temperature varies based on ambient temperature and particulars of the wall board and structure in which the mold is located. The processor 905 also uses the temperature sensor 930 to monitor the temperature and to ensure that the desired temperature is maintained for the desired duration of time. The processor 905 also uses the timer 935 to monitor the time duration.

In addition to mold remediation, the embodiments described herein can be used in any application in which it is desirable to heat one side of a surface, but not the other. Unlike use of a heat gun or other conduction-based heating system, induction heating is controllable through placement of the ferromagnetic material heats up in response to radiation. For example, it may be desirable to heat only a rear side of a wall to protect a valuable painting or other artwork that is displayed on a front side of the wall. The rear side of the wall can be heated by placing ferromagnetic material on or adjacent to the rear side of the wall and passing electromagnetic radiation through the ferromagnetic material. As a result, there is little or no heat experienced by the front side of the wall. This technique can be used in any situation in which is desirable to heat one side of a surface but not the other.

In another illustrative embodiment, induction heating can be used to activate and/or cure an adhesive substance to bond materials together. For example, various types of flooring materials are installed via an adhesive. However, traditional installations are limited by the small amount of adhesive that can be applied at a given time to prevent unintentional setting. For example, it is typically not possible to apply adhesive to an entire floor and then install flooring over the entire floor because the installers are unable to avoid contact with the adhesive, which is messy and reduces the effectiveness of the adhesive. Additionally, the adhesive may begin to set up (i.e., harden) before the installation is complete, which necessitates the difficult process of removing the set adhesive and reapplying new adhesive. As a result, a typical installation involves applying adhesive to a small portion of the floor and then quickly (i.e., prior to the adhesive setting) installing the flooring material to the small portion of the floor. This time consuming process is repeated until the entire floor is covered.

The difficulties associated with a traditional flooring installation can be avoided by using a heat activated adhesive and an induction heating system. Any type of heat activated or heat cured adhesive known in the art may be used such as epoxy, laminating adhesive, water-based adhesive, polyurethane, emulsion adhesive, hot melt adhesive, etc. In one embodiment, ferromagnetic particles are incorporated into the heat activated adhesive and, upon application of electromagnetic radiation from an EM source, the ferromagnetic particles are heated, thereby causing the adhesive to activate at set. The ferromagnetic particles can be nanoparticles, micro-particles, etc. In an alternative embodiment, ferromagnetic sheets can be applied over the installed flooring and the sheets can be heated with EM radiation to activate an adhesive applied underneath the installed flooring.

As an example, a heat activated adhesive is applied to a subfloor onto which flooring is to be installed. The application of the adhesive can be performed using any techniques known in the art such as spraying, rolling, etc. The flooring is then installed on top of the heat activated adhesive using any techniques known in the art. An induction heating system is used to activate the adhesive to bond the installed flooring to the subfloor. The induction heating system can include one or more of a processor, memory, transceiver, interface, electromagnetic radiation source, and a temperature sensor.

In an illustrative embodiment, the electromagnetic radiation source of the induction heating system is used to activate the adhesive by directing radiation at ferromagnetic particles embedded in the adhesive. Alternatively, the adhesive may not include particles and ferromagnetic sheets (or other ferromagnetic material) can be temporarily applied over the installed flooring. In such an implementation, the radiation is directed to the sheets (or other ferromagnetic material), which causes them to heat up. The heat is transferred from the sheets to the installed flooring and to the heat activated adhesive. As a result, the adhesive is heated and activated, which bonds the flooring to the subfloor.

A temperature sensor of the induction heating system is used to directly or indirectly detect the temperature of the heat cured adhesive to ensure that the proper temperature for activation/curing is achieved. The system can also include a timer that is used to monitor the amount of time which the proper temperature is maintained. For example, some heat activated adhesives need to be heated for a specified duration of time to ensure proper activation and curing. The processor of the system is used to control the various components to ensure that the specified temperature and time duration is used.

It is noted that the installation of flooring is just one example for the use of an induction heating system to activate an adhesive, and that the application is not so limited. In alternative embodiments, the induction heating system can be used to activate a heat activated adhesive for any other application such as component assembly, hanging objects on a wall, woodworking, etc. In another embodiment, the induction heating system can be used to perform soldering to adhere materials to one another. For example, electromagnetic radiation can be directed from an EM source to solder (e.g., lead, tin, copper, etc.) to heat and melt the solder, which can then be used to adhere materials as known in the art. If the solder material is not ferromagnetic, ferromagnetic particles can be implanted into the solder material such that the radiation heats the implanted particles, thereby heating and melting the solder.

The induction heating systems described herein can also be used to detect wires and/or pipes behind walls. The wires and/or pipes can be made from ferromagnetic materials and/or can be wrapped with a ferromagnetic material or have ferromagnetic particles incorporated therein. Specifically, EM radiation is directed at a wall and a temperature sensor is used to detect whether there is a temperature increase behind the wall. The temperature sensor can be used on the accessible side of the wall or placed behind the wall via a small hole in the wall. The EM radiation causes the pipe/wire to heat up, which is detected by the temperature sensor and indicative that a pipe/wire is present.

The induction heating systems can also be used to provide heat to ferromagnetic objects such as a metallic structure surrounding a beehive during the winter to keep the beehive warm. The induction systems can similarly be used to heat water pipes to prevent them from freezing, to heat a metallic shed, a fish pond, or other structure, etc. Notably, the induction heating systems can be used in any application in which wireless heating is desired. For example, it may be undesirable to run electrical wires into a fish pond. Induction heating can be used to heat the fish pond without the need to run wires. For example, one or more ferromagnetic rods can be placed into the water and heated via induction. The rods then pass the heat to the water in the pond via conduction, heating the water and preventing it from freezing. A partial or complete covering over the pond can also be used. The covering can be made of ferromagnetic material, which is heated by induction, thereby heating the water through conduction.

As discussed above, the induction heating systems can be used in any application in which wireless heating is desired. Induction heating can be used to heat a blanket, a bed, or a portion of a bed. For example, a blanket containing ferromagnetic particles can be placed on or under a bed and heated with induction heating. Doghouses, sheds, storage containers, etc. that are not wired for electricity can also be heated through induction, as long as an electromagnetic radiation source can be activated in proximity to the object being heated. In one embodiment, the electromagnetic radiation source is battery-operated, and can be used off of the electrical grid to provide induction heating.

In some embodiments, a portable or mobile induction heating system can be used in an office or home setting to heat a space or items such as food. As an example, the portable induction heating system can also be used to heat food in place of a microwave or toaster oven. The portable induction heating system can include an electromagnetic source to generate radiation used to heat one or more ferromagnetic components of the system. Once heated through induction, the ferromagnetic components transfer the heat to food which is to be warmed/cooked and/or into the environment to heat a space. As discussed in more detail below, the portable induction heating system can be in the form of a space heater, a cooktop, a grill, a pizza oven, etc. The portable induction heating system can be used in homes offices, schools, campers, etc. to provide a flame free alternative to traditional cooking and heating.

In traditional induction heating systems, an electromagnetic source heats a metallic component that is not an integral part of the heating system. For example, a traditional induction cooktop does not include a surface that gets hot, but instead heats a pot/pan that rests upon the cooktop. In at least some embodiments, the proposed portable induction heating system includes one or more integral metallic components that are heated, and which in turn are used to heat a space, food, or other items. The one or more integral metallic components can be in the form of a flat cooking/heating surface, a grill grate, an oven/box configuration, a heating register, etc. In another illustrative embodiment, the induction heating system can include interchangeable integral metallic components such that the heating system can have a variety of different functions.

Figure 10:
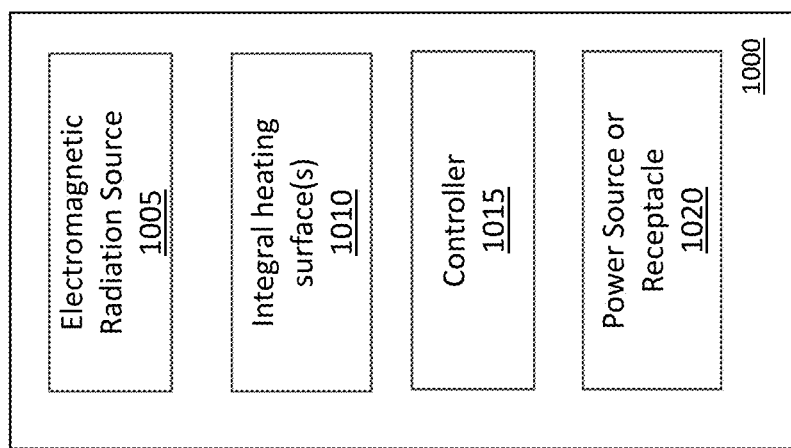
FIG. 10 is a block diagram of a portable induction heating system in accordance with an illustrative embodiment.

FIG. 10 is a block diagram of a portable induction heating system 1000 in accordance with an illustrative embodiment. The portable induction heating system 1000 includes an electromagnetic radiation source 1005, one or more integral heating surfaces 1010, a controller 1015, and a power source or receptacle 1020. In alternative embodiments, the portable induction heating system can include fewer, additional, and/or different components. The electromagnetic radiation source 1005 can be any type of radiation source that is able to facilitate induction heating of a ferromagnetic material that is in the presence of the radiation. The power source or receptacle 1020 can be a battery, one or more capacitors, or other source of power that is able to run the electromagnetic radiation source 1005 and the controller 1015. In one embodiment, the battery can be a rechargeable battery that enables mobility and off-grid use of the system. The power source or receptacle 1020 can also include a plug (or socket) that is configured to receive power from an external source such as a power outlet or direct wire hookup.

In an illustrative embodiment, the electromagnetic radiation source 1005, the controller 1015, and the power source or receptacle 1020 are all incorporated into a portable base unit of the system. In some embodiments, the portable base of the system includes a mounting surface that is configured to receive a plurality of different interchangeable heating surfaces depending on the application to be performed. For example, as discussed in more detail below, the heating surfaces can include a grill heating surface, an oven heating surface (or chamber), a space heater (or radiator) heating surface, etc.

The controller 1015 can be a digital or analog controller that controls the magnitude of radiation output by the electromagnetic radiation source 1005. The magnitude of the radiation output by the system in turn controls the amount of heat generated at the one or more integral heating surfaces 1010. In some embodiments, the controller 1015 can be computerized, and can include components such as a processor, memory, interface, transceiver, etc. to perform heating operations and temperature control.

In an illustrative embodiment, different types of heating surfaces 1010 that can be installed on the system may operate in accordance with different sets of operating instructions. The memory of the controller 1015 can be used to store operating algorithms for different types of integral heating surfaces 1010. For example, a grill heating surface can be controlled in accordance with a first set of operating instructions stored in the memory, a pizza oven heating surface can be controlled in accordance with a second set of operating instructions stored in the memory, and a radiator heating surface can be controlled in accordance with a third set of operating instructions stored in the memory. The processor of the controller 1015 is used to execute the operating instructions corresponding to the installed heating surface. As an example, a set of operating instructions for the grill heating surface can include, based on a user setting, focusing the EM radiation onto only a portion of the grill grates so that only a portion of the grill grates become hot. Conversely, a set of operating instructions for a radiator heating surface can including heating an entire base of the radiator such that the entire radiator heating surface generates heat.

In some embodiments, the controller 1015 is able to automatically detect what type of integral heating surface is installed on the system and, based on the detection, select the appropriate set of operating instructions that are specific to the detected heating surface. The controller 1015 can automatically detect the installed heating surface by reading a tag/chip incorporated into the heating surface, by reading a bar code or text on the heating surface, using near field communication (NFC), etc. In an alternative embodiment, a user can enter the type of installed heating surface via an interface of the controller 1015 such that the system knows which surface is attached. In an alternative embodiment, all of the different types of heating surfaces may operate in accordance with the same set of operating instructions and determination of the type of heating surface may not be performed.

Figure 11B:
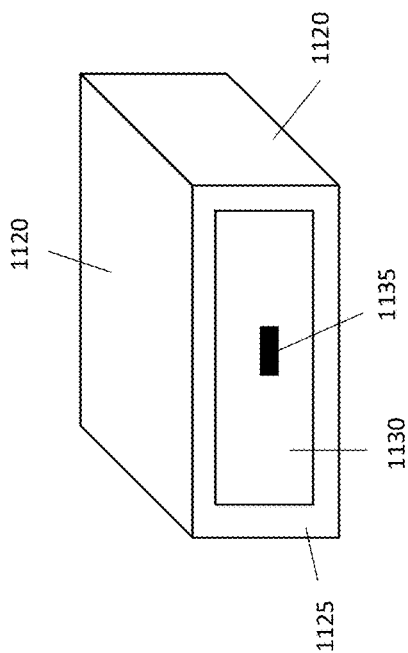
FIG. 11B is a front perspective view of an oven heating surface in accordance with an illustrative embodiment.
Figure 11A:
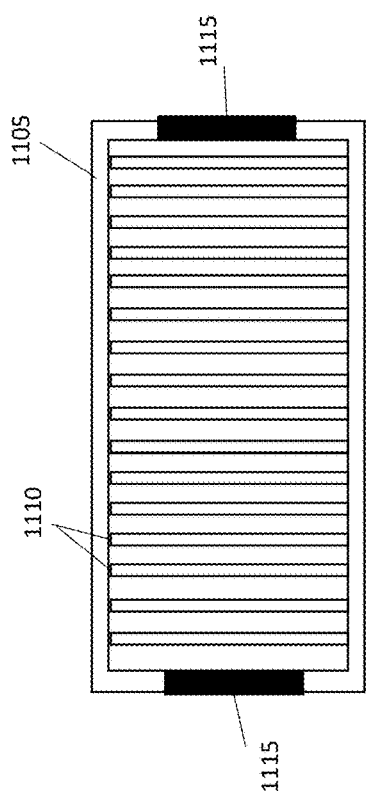
FIG. 11A depicts a grill grate heating surface in accordance with an illustrative embodiment.
Figure 11D:
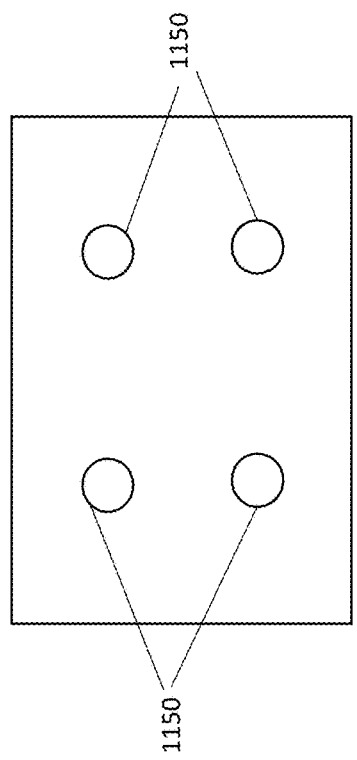
FIG. 11D is a top view of a flat plate heating surface in accordance with an illustrative embodiment.
Figure 11C:
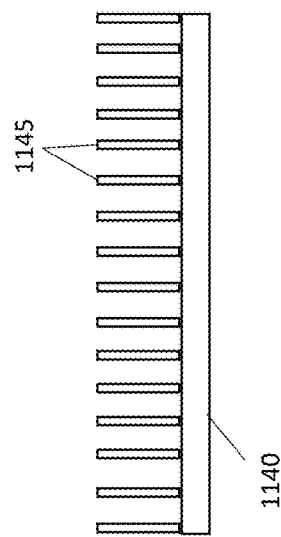
FIG. 11C is a side view of a radiator heating surface in accordance with an illustrative embodiment.

The one or more integral heating surfaces 1010 can include a flat cooking/heating surface, a grill grate, an oven/box configuration, a heating register, etc. FIG. 11 depicts various heating surfaces that can be interchangeably mounted to the proposed induction heating system in accordance with illustrative embodiments. Specifically, FIG. 11A depicts a grill grate heating surface in accordance with an illustrative embodiment. FIG. 11B is a front perspective view of an oven heating surface in accordance with an illustrative embodiment. FIG. 11C is a side view of a radiator heating surface in accordance with an illustrative embodiment. FIG. 11D is a top view of a flat plate heating surface in accordance with an illustrative embodiment.

As shown in FIG. 11A, the grill grate heating surface includes a frame 1105 that surrounds a plurality of grates 1110 that extend between walls of the frame 1105. In an illustrative embodiment, at least the grates 1110 are made from a ferromagnetic material that heats via induction. The frame 1105 can be ferromagnetic or non-ferromagnetic depending on the implementation. In an illustrative embodiment, the grill grate heating surface can be removably mounted to a base of the system that includes the electromagnetic radiation source 1005, the controller 1015, and the power source or receptacle 1020 described with reference to FIG. 10. In some embodiments, the grill grate heating surface can also include a drip pan positioned between the base of the system and the grates 1110 such that any drippings from cooking on the grates 1110 do not land on the base. Additionally, one or more handles 1115 are included such that a user is able to move the grill grate heating surface. In an illustrative embodiment, the one or more handles 1115 are made from a non-ferromagnetic material such that the handles do not heat up due to induction when the grill grate heating surface is being used. As a result, the user can remove the entire grill grate heating surface along with any prepared food with a low risk of getting burned. Any of the other heating surfaces described herein can similarly include one or more non-ferromagnetic handles that allow the user to safely transport the heating surface after use.

The oven heating surface of FIG. 11B includes a plurality of surfaces 1120 (i.e., top, bottom, sides, and rear) that can be made from ferromagnetic material such that the surfaces heat via induction, and a cavity formed by the surfaces acts as an oven or other heating chamber. For example, the oven heating surface can be configured as a pizza oven. The oven heating surface also includes a front surface 1125 that includes a door 1130 and a handle 1135 on the door. In some embodiments, the door 1130 can be hinged to the front surface 1125 similar to a standard oven door. In alternative embodiments, the door 1130 may be connected to a food placement surface (e.g., oven rack or pizza stone), and the door 1130 and food placement surface can be configured to slide out from the front surface 1125 similar to a standard pizza oven. The front surface 1125 and door 1130 can be made from a ferromagnetic material or a non-ferromagnetic material, depending on the implementation. The handle 1135 on the door 1130 can be made from a non-ferromagnetic material such that a user is less likely to receive a burn when opening the door 1130. In an illustrative embodiment, the oven heating surface can be removably mounted to a base of the system that includes the electromagnetic radiation source 1005, the controller 1015, and the power source or receptacle 1020 described with reference to FIG. 10.

The radiator heating surface of FIG. 11C includes a base 1140 and a plurality of fins 1145. In an illustrative embodiment, both the base 1140 and the plurality of fins 1145 are made from a ferromagnetic material such that both components are heated via induction. Due to its proximity to the electromagnetic radiation source incorporated into the system base, the base 1140 of the radiator heating surface will heat more via induction than the fins 1145. Since the fins 1145 are integrally connected to the base 1140, the fins 1145 will be heated by both induction (i.e., as a result of radiation from the source) and conduction (i.e., due to contact with the base 1140). As with the other heating surfaces, the radiator heating surface is configured to be removably mounted to the base of the system described with reference to FIG. 10. The radiator heating surface can be used to heat an enclosed space, such as an office, bedroom, bathroom, classroom, etc.

The flat plate heating surface of FIG. 11D includes a uniform heating surface that is configured to generate heat for heating food or an environment. The flat plate heating surface is made from a ferromagnetic material and is heated via induction as described herein. As with the other heating surfaces, the flat plate heating surface is configured to be removably mounted to the base of the system described with reference to FIG. 10. As shown, the flat plate heating surface includes a plurality of heat sensors 1150. In alternative embodiments, fewer or additional heat sensors may be used. Also, any of the other heating surfaces described herein can similarly include one or more heat sensors to help control operation of the system. The heat sensors 1150 can be mounted on an inner or outer surface of the heating surface (e.g., the flat plate, the grill grates, the oven walls, the radiator base or fins, etc.). The heat sensors 1150 can also be mounted internal to a portion of the heating surface (i.e., embedded in one or more portions of the heating surface).

The heat sensors 1150 can be used as part of a feedback loop to provide the base of the system with information regarding the temperature of the heating surface such that efficient and accurate temperature control can be performed. For example, if the user desires that the flat plate heating surface be set at 200 degrees Fahrenheit (F), a transceiver incorporated into the system controller can receive temperature readings from each of the heat sensors 1150. Responsive to temperature readings less than 200 degrees F., the system controller can automatically increase the amount and/or magnitude of the electromagnetic radiation being used to increase the temperature. Response to temperature readings more than 200 degrees F., the system controller can automatically decrease the amount and/or magnitude of the electromagnetic radiation being used to decrease the temperature of the flat plate heating surface. The heat sensors 1150 can be configured for wireless signal transmission that is received by the transceiver of the system controller. Alternatively, the heating surface can plug into the base of the system to provide a wired connection between the heat sensors and the controller for conveyance of temperature and other information.

In an illustrative embodiment, the interchangeable heating surfaces can readily mount/dismount to/from a mounting surface of the base unit of the system without the use of tools. For example, in one embodiment, a bottom surface of the heating surfaces can include one or more ridges or posts that fit into one or more corresponding grooves or holes formed into the base to securely hold the heating surface to the base. Alternatively, the ridges or posts can be on the base and the bottom of the heating surface can include one or more corresponding valleys or holes to secure the heating surface to the base. In alternative embodiments, one or more clamps, straps, latches, etc. may also be used to secure a heating surface to the mounting surface of the base.

FIG. 12A is a side view of a base unit 1200 of a portable induction heating system in accordance with an illustrative embodiment. FIG. 12B is a side view of a heating surface 1220 that mounts to the base unit 1200 in accordance with an illustrative embodiment. The base unit 1200 includes an EM source, a power source/receptacle, a controller, and a mounting surface 1205 that is configured to receive a heating surface. The mounting surface includes grooves 1210 that are configured to receive corresponding ridges 1225 on a bottom of the heating surface 1220. In one embodiment, four grooves (i.e., one in each corner) can be used. Alternatively, two grooves that run the entire width of the mounting surface 1205 may be used. Alternatively, instead of grooves, the mounting surface 1205 can include holes that are configured to receive posts mounted to the bottom of the heating surface. The base unit 1200 also includes clamps 1215 that extend from the side of the base unit 1200 up past the top of the mounting surface 1205. In an illustrative embodiment, the clamps may be flexible such that a rod portion of the clamps 1215 bends outward from the sides of base unit 1200 until the heating surface 1220 is in place. A protrusion mounted to the rod portion of the clamps can mate with a groove or hole 1230 in a side wall of the heating surface 1220 to help secure the heating surface 1220 to the base unit 1200. In alternative embodiments, only the grooves/ridges may be used to secure the components to one another. In another alternative embodiment, only the clamps may be used to secure the components to one another. In some embodiments, a wired plug or socket connection may also be made between the heating surface 1220 and the base unit 1200. The wired plug or socket connection can allow the base unit 1200 to receive temperature and other information from the heating surface 1220.

The embodiments described above for a portable induction heating system have been described in terms of a base unit that is configured to accommodate a plurality of different interchangeable heating surfaces depending on the user's desired application. In alternative embodiments, the any of the heating surfaces described herein can be permanently mounted onto the base unit such that the system is dedicated to a single heating surface.

The portable induction heating systems described herein can be used in place of a microwave, space heater, cooktop, grill, and/or oven in spaces where flame heat is not desirable or allowed. For example, many city buildings prohibit the use of portable cooking systems with an open flame. The portable induction heating system is ideal for use in such locations, including apartment buildings, office buildings, schools, dorm rooms, etc.

In another embodiment, a system can include a plurality of ferromagnetic elements and one or more electromagnetic sources. The one or more electromagnetic sources can be configured to selectively heat a subset of the plurality of ferromagnetic elements in some embodiments. Alternatively, all of the ferromagnetic elements can be heated simultaneously. In some embodiments, different ferromagnetic elements can be heated to different degrees by altering the intensity of the electromagnetic radiation from the one or more electromagnetic sources and by specifically targeting different ferromagnetic elements.

Figure 13:
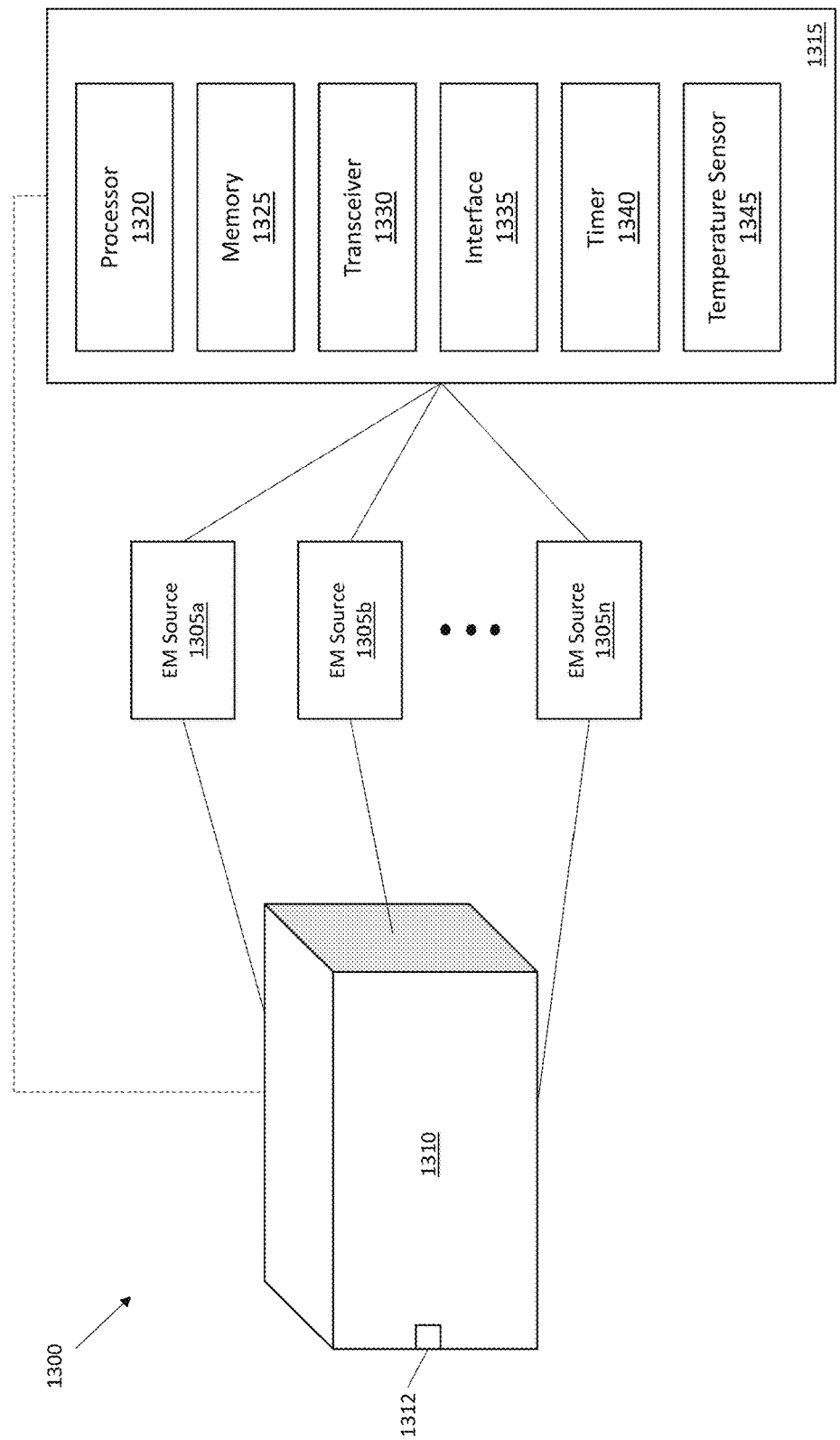
FIG. 13 depicts a system for targeted induction heating in accordance with an illustrative embodiment.

FIG. 13 depicts a system 1300 for targeted induction heating in accordance with an illustrative embodiment. The system 1300 includes a plurality of electromagnetic sources 1305a . . . n and a container 1310 that is positioned in the path of the electromagnetic sources 1305a . . . n. In an illustrative embodiment, the container 1310 is made from a non-ferromagnetic material and includes a plurality of ferromagnetic elements, as described in more detail below. The system 1300 also includes a computing system 1315 that controls the plurality of electromagnetic sources 1305a . . . n. In some embodiments, the computing system can also be in communication with the container 1310.

In one embodiment, the container 1310 can be a food container or a cooking vessel. Alternatively, the container can be any other type of container used to heat items such as a clothes dryer, etc. The container 1310 can include one or more partitions that create a plurality of chambers in the container 1310. Each of the chambers can be used to heat a different type of food, and the different chambers can be heated to different temperatures. Alternatively, the container 1310 may include a single chamber.

The ferromagnetic elements can be positioned on the inside or outside of the container and used to heat contents of the container 1310. For example, one or more ferromagnetic elements may be mounted to an external surface (wall) of the container 1310 and/or one or more ferromagnetic elements can be mounted to an internal surface (wall) of the container 1310. In some embodiments, the container 1310 can have an outer wall and an inner wall, and one or more ferromagnetic elements can be positioned in between the outer wall and the inner wall. In other embodiments, the container 1310 can include a lid, and one or more ferromagnetic elements can be mounted to the lid. One or more ferromagnetic elements can also be positioned within an object that is placed into the container 1310. For example, a ferromagnetic element can be partially or fully embedded into a piece of food that is placed into the container 1310 for heating/cooking.

In another illustrative embodiment, the container 1310 is configured such that the ferromagnetic element(s) can be moved to different positions within/on the container 1310 depending on the user's needs. For example, in some situations it may be desirable to have one or more ferromagnetic elements in a first chamber of the container 1310 and no ferromagnetic elements in a second chamber of the container 1310. As another example, it may be desirable to have one ferromagnetic element in the first chamber and a plurality of ferromagnetic elements in the second chamber. The container 1310 is thus configurable depending on the heating needs of the user.

The ferromagnetic elements can be mounted in/on the container 1310 using one or more hooks positioned on an interior of the container 1310, one or more hooks positioned on an exterior of the container 1310, one or more slots formed in between an outer side wall and an inner side wall of the container 1310, one or more slots formed between an outer bottom wall and an inner bottom wall of the container 1310, one or more slots formed between an outer surface of the lid/top of the container 1310 and an inner surface of the lid/top, by one or more stands that rest on a bottom surface of the container 1310, etc. Alternatively, the ferromagnetic elements can be placed into the container 1310 without any mount/holder such that the elements rest on a desired portion of the bottom wall of the container. The ferromagnetic elements can also be partially or wholly embedded into food or another item that is to be heated in the container 1310. In another embodiment, the ferromagnetic elements can be in the form of receptacles that can be positioned within the container 1310. The receptacles can be configured to partially or wholly contain items to be heated, such as food. In another embodiment, the ferromagnetic element can be embedded in the food (or other item to be heated) by a manufacturer of the food/item. In such an embodiment, a user can place the food/item and embedded ferromagnetic element into the container 1310 for heating as described herein.

In an alternative embodiment, the container 1310 may be fabricated such that the walls, bottom, and/or lid are made from both ferromagnetic material and non-ferromagnetic material. The non-ferromagnetic material can be wood, plastic, rubber, aluminum, etc. The container 1310 can include multiple chambers and the different chambers of the container 1310 can be heated differently by targeting the different areas of ferromagnetic material with varying amounts of electromagnetic radiation.

As shown in FIG. 13, the container 1310 also includes a sensor 1312. In alternative embodiments, the sensor 1312 may not be included. In one embodiment, the sensor 1312 can be a temperature sensor used to detect temperature within/on the container 1310, and can be configured to convey the temperature information to the computing system 1315 for use as feedback in determining how to control the electromagnetic sources 1305a . . . n going forward. The temperature information can be conveyed to the computing system 1315 via a wired or wireless connection, depending on the implementation. The sensor 1312 can alternatively include one or more sensors, each of which is positioned in a mounting location for a ferromagnetic element. The sensor(s) 1312 can detect presence of a mounted ferromagnetic element at a given location (through pressure/weight, electronic communication with the element, etc.), and can convey this location information to the computing system 1315 such that the computing system 1315 knows where to direct the targeted electromagnetic radiation. In some embodiments, the container 1310 can include a plurality of sensors for sensing temperature(s) within/on the container and/or location(s) in which ferromagnetic elements are mounted in/on the container 1310.

The system also includes the electromagnetic sources 1305a . . . n, where n can be any number. In one embodiment, each of the electromagnetic sources 1305a . . . n can be controlled to heat one or more ferromagnetic elements positioned in/on the container 1310. The electromagnetic sources 1305a . . . n can be any type of electromagnetic wave generators. In an illustrative embodiment, each of the electromagnetic sources 1305a . . . n has an adjustable intensity such that the intensity of the electromagnetic radiation can be controlled by the computing system 1315. Alternatively, the electromagnetic sources may not include adjustable intensity. In such an embodiment, different electromagnetic sources can have different preset intensities, and the electromagnetic source to be used for a given heating application can be specific to the desired intensity for the application. In some embodiments, the electromagnetic sources 1305a . . . n can each include an actuator that enables the electromagnetic source to move such that specific ferromagnetic elements can be targeted (i.e., without significantly affecting non-targeted ferromagnetic elements).

In another embodiment, the system 1300 may include a single electromagnetic source with adjustable intensity. In such an embodiment, the single electromagnetic source can be used to heat a plurality of different electromagnetic elements to a plurality of different temperatures. In one embodiment, the single electromagnetic source can be configured to move (e.g., via an actuator) such that different ferromagnetic elements can be specifically targeted with different amounts of radiation and/or for different durations of time.

The computing system 1315 includes a processor 1320, a memory 1325, a transceiver 1330, an interface 1335, a timer 1340, and a temperature sensor 1345. In alternative embodiments, the computing system 1315 can include fewer, additional, and/or different elements. The computing system 1315 is used to control the electromagnetic sources 1305a . . . n. In some embodiments, the computing system can also be in direct or indirect communication with the container 1310, as indicated by the dashed line in FIG. 13. In some embodiments, the computing system 1315 can be incorporated into one (or all) of the electromagnetic sources 1305a . . . n.

The processor 1320 of the computing system 1315 is used to execute computer-readable instructions stored in the memory 1325. The computer-readable instructions can include instructions to align each of the electromagnetic sources 1305a . . . n with one or more ferromagnetic elements such that the one or more ferromagnetic elements are heated, to individually turn the electromagnetic sources 1305a . . . n on/off, to control an amount of time that each of the electromagnetic sources 1305a . . . n is on/off, to control an intensity of each of the electromagnetic sources 1305a . . . n, to monitor a temperature of the one or more ferromagnetic elements, etc.

In addition to storing the aforementioned computer-readable instructions, the memory 1325 can also be configured to store an operating system, communication algorithms, positional information regarding the ferromagnetic elements, identification information for the ferromagnetic elements, etc. For example, the memory 1325 can store the specific location of each ferromagnetic element in the container, and as discussed herein those locations can change because the container 1310 can be configurable with respect to placement of the elements. The locations of the elements within/on the container 1310 can be entered by a user into the computing system via the interface 1335. Alternatively, each of the ferromagnetic elements may include a tag, transceiver, or other communication component that is able to communicate with the transceiver 1330 of the computing system 1315. In such an embodiment, the processor 1320 can use the transceiver 1330 to obtain location information from each of the ferromagnetic elements and can store the location information in the memory 1325. The location information can be positional information regarding element receiving locations of the container 1310, such as slot 1, slot 2, slot 3, etc., or first hook, second hook, third hook, etc.

The transceiver 1330 is configured to communicate with the electromagnetic sources 1305a . . . n through a wired connection or a wireless connection. The transceiver 1330 can be used by the processor to send operating instructions to the electromagnetic sources 1305a . . . n and/or to receive feedback from the electromagnetic sources 1305a . . . n. The transceiver 1330 can also be used to communicate with the one or more ferromagnetic elements as discussed above.

The interface 1335 enables the user to enter information into the computing system 1315 and/or to monitor progress of heating within the container 1310. The interface 1335 can include a mouse, display, touchscreen, keyboard, microphone, speaker, etc. The information entered by the user can include a desired amount of time for each of the electromagnetic sources 1305a . . . n to operate, a desired intensity for each of the electromagnetic sources 1305a . . . n to use when emitted electromagnetic radiation, which ferromagnetic element(s) should be targeted by which electromagnetic sources 1305a . . . n, desired temperature(s) for different portions of the container 1310 and/or for different ferromagnetic elements in/on the container 1310, etc.

The timer 1340 can be used to monitor and control an amount of time that the electromagnetic sources 1305a . . . n remain on (i.e., emitting radiation) and off (i.e., not emitting radiation) to control heating of the ferromagnetic elements. The timer 1340 can also be used to monitor an amount of time that food/items have been heated with the container 1310.

The temperature sensor 1345 can include one or more temperature sensors that are used to monitor temperature(s) associated with the container 1310. The monitored temperature(s) can include the temperatures of individual ferromagnetic elements, the internal temperature of food or other items within the container 1310, the ambient temperature within the container 1310, a temperature on the exterior of the container 1310, etc. In some embodiments, the temperature sensor(s) can be incorporated into the ferromagnetic elements, and the ferromagnetic elements can be configured to transmit their temperatures to the computing system 1315. The computing system 1315 can use the temperature feedback to control the electromagnetic sources 1305a . . . n to achieve a desired temperature of the food/item being heated. Temperature sensor(s) can also be embedded in/on the container 1310 and configured to transmit temperature information of the container 1310 to the computing system 1315. A probe temperature sensor can also be used to monitor the internal temperature of food/items within the container. In an alternative embodiment, the temperature sensor 1345 can include an infrared detection system that is configured to use infrared radiation to detect the temperature of specific ferromagnetic elements and/or specific locations of the container 1310.

Figure 14B:
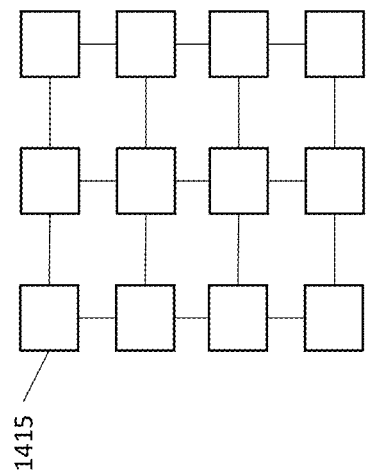
FIG. 14B depicts an array that includes a plurality of ferromagnetic elements in accordance with an illustrative embodiment.
Figure 14A:
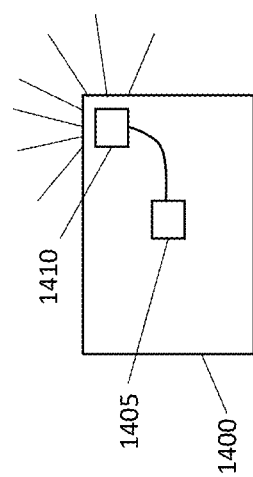
FIG. 14A depicts a ferromagnetic element in accordance with an illustrative embodiment.

FIG. 14A depicts a ferromagnetic element 1400 in accordance with an illustrative embodiment. The ferromagnetic element 1400 includes a temperature sensor 1405 positioned in a center of the element. Alternatively, the temperature sensor 1405 may be positioned elsewhere such as off-center, on an internal edge of the ferromagnetic element 1400, on an external surface of the ferromagnetic element 1400, etc. In alternative embodiments, the ferromagnetic element 1400 may not include a temperature sensor. The ferromagnetic element 1400 also includes a transceiver 1410 which can be used to transmit temperature information to a computing system that is monitoring the temperature. The transceiver 1410 can also be used to transmit identification information corresponding to the ferromagnetic element 1400 such that the computing system knows which element it is communicating with. The transceiver 1410 can also be configured to transmit location information that informs the computer where the ferromagnetic element is positioned within/on the container 1310. In such an embodiment, the container 1310 may include mounting locations for ferromagnetic elements, and each mounting location in/on the container 1310 can include a sensor that informs the transceiver 1410 of the location in which the element is mounted. The transceiver 1410 can receive this location information from the sensor and pass it on to the computing system.

The ferromagnetic element 1400 depicted in FIG. 14A is in the form of a rectangular parallelepiped. In alternative embodiments a different shape may be used such as cube, sphere, pyramid, etc. Additionally, different shapes and/or sizes can be used for different ferromagnetic elements to control the amount of the heat that they deliver (i.e., a larger element has more surface area and will deliver more heat than a smaller element). Information regarding the size/shape of the individual ferromagnetic elements 1400 can be provided to the computing system using any of the communication techniques described herein.

FIG. 14B depicts an array that includes a plurality of ferromagnetic elements 1415 in accordance with an illustrative embodiment. While the array is shown with 12 elements in a rectangular pattern, it is to be understood that different numbers of elements and/or pattern shapes may be used. The array can be placed into a wall of a container (e.g., side wall, bottom wall, top wall/lid). For example, the array can be placed in between a double wall of the container that includes an interior wall and an exterior wall. The array can alternatively be positioned in an interior of the container. In some embodiments, one or more arrays can be positioned in/on the container such that the individual elements are able to heat multiple chambers of the container to varying degrees. The individual elements can be selectively targeted and heated by the electromagnetic source(s) such that the user is able to accurately control the heating of different items within the container to different temperatures.

In another embodiment, an induction heating system includes one or more ferromagnetic elements that move into and out of EM radiation emitted by an EM radiation source to control the temperature of the element(s). The induction heating system with moving ferromagnetic elements can be implemented as a cooking vessel, a heating system for a room or building, etc. In an illustrative embodiment, the EM radiation source can be mounted such that it emits EM radiation at a specific emission location/area of the system. The ferromagnetic elements move into this specific location/area to be heated and move out of this location/area to cool down. In some embodiments, the ferromagnetic elements and/or other portion of the system include temperature sensors, and the system includes an automated movement system to move the elements into and out of the EM radiation based on their temperature. In other embodiments, individual ferromagnet elements may be configured to move themselves into and out of the radiation such that the elements maintain a desired temperature.

FIG. 15A is a first side view of an induction heating system with a moving ferromagnetic element in accordance with an illustrative embodiment. FIG. 15B is a second side view of the induction heating system with the moving ferromagnetic element in accordance with an illustrative embodiment. As shown, an electromagnetic radiation source 1500 is mounted to a side of a base 1505 of the system. Any type of EM radiation source can be used. The base 1505 can be in the form of a cooking vessel, a portable heater, or any other type of heat generating system. Mounted to the base is an element controller 1510 that is connected to a ferromagnetic element 1515 by a cable 1520. Dashed lines in the figures indicate an emission area (i.e., band) 1525 of the base 1505 that is subjected to electromagnetic radiation from the EM radiation source 1500. When the ferromagnetic element 1515 is positioned within the emission area 1525 (e.g., as shown in FIG. 15A), it is thus subjected to the EM radiation from the EM radiation source 1500 and heated as a result. When the ferromagnetic element 1515 is positioned outside of the emission area 1525 (e.g., as shown in FIG. 15B), it does not receive the EM radiation and is therefore not heated. While the emission area 1525 is depicted as a uniform band, in real world implementations, the emission area 1525 may be a non-uniform band or other area.

As discussed, the base 1505 of the induction heating system can be in the form of a cooking vessel. In such an implementation, the cooking vessel can be a double-walled cooking vessel and the ferromagnetic element 1515, cable 1520, and/or element controller 1510 can be positioned between an inner wall and an outer wall of the cooking vessel. Alternatively, the cooking vessel may be a single wall vessel, and the ferromagnetic element 1515, cable 1520, and/or element controller 1510 can be positioned on an exterior wall surface of the cooking vessel such that these components do not contact the food/contents within the cooking vessel. In another alternative embodiment, the ferromagnetic element 1515, cable 1520, and/or element controller 1510 can be positioned on an interior wall surface of the cooking vessel such that the ferromagnetic element 1515 is in contact with the contents of the vessel. In one embodiment, the base 1505 can act as a radiator that is heated by the ferromagnetic element 1515 to heat an area such as a bedroom, office, etc.

The EM radiation source 1500 is shown mounted on a side of the base 1505 such that the emitted radiation from the EM radiation source 1500 forms the emission area 1525 as a horizontal band across the base 1505. In alternative embodiments, the EM radiation source 1500 can be positioned on a bottom of the base or on a top of the base 1500. In other alternative embodiments, the EM radiation source 1500 can be mounted such that it emits radiation at a diagonal angle relative to a bottom surface of the base 1500, wherein the diagonal angle can be 10°, 20°, 45°, 60°, etc. In some embodiments, multiple EM radiation sources 1500 can be mounted to or proximate to the base to emit the radiation. For example, two or more EM radiation sources can be mounted opposite one another (i.e., at a same elevation of the base 1505) to form the emission area 1525. As discussed in more detail below, the system can also include a plurality of emission areas formed by placement of different EM radiation sources 1500 about the base 1505. The EM radiation source(s) 1500 can be mounted directly to the base 1505 using fasteners, adhesive, clips, slots, etc. In an alternative embodiment, the EM radiation source(s) 1500 can be mounted to a surface or holder that is configured to receive the base 1505.

The element controller 1510 is mounted to the base 1505 and used to raise and lower the ferromagnetic element 1515. As such, the ferromagnetic element 1515 can be placed into the emission area 1525 such that it is heated by the radiation emitted into the emission area 1525. The ferromagnetic element 1515 can also be removed from the emission area 1525 such that it is no longer heated responsive to the radiation, and thus begins to cool down. In some embodiments, the base 1505 includes a temperature sensor 1530 that is used to monitor the temperature of the contents of the base 1505. The temperature sensor 1530 can include or be in communication with a processor that controls operation of the element controller 1510. If the temperature sensor 1530 determines that the contents of the base 1505 have exceeded a threshold temperature, the element controller 1510 moves the ferromagnetic element 1515 out of the emission area 1525 such that further heating does not occur. If the temperature sensor 1530 determines that the contents of the base 1505 are not yet at a desired temperature, the element controller 1510 can move the ferromagnetic element 1515 into the emission area 1525. Similarly, if the ferromagnetic element 1515 is removed from the emission area 1525 because the threshold temperature was exceeded, the element controller 1510 can move the ferromagnetic element 1515 back into the emission area 1525 if the temperature of the contents of the base 1505 drops below the desired temperature. In another embodiment, each individual ferromagnetic element 1515 can include a temperature sensor and the elements can be controlled (i.e., placed into and moved out of the emission area 1525) based on the temperature of the element.

The element controller 1510 can be mounted to the base 1505 using fasteners, adhesive, clips, slots, etc. In one embodiment, the element controller 1510 includes a spindle upon which the cable 1520 is wound. As the spindle rotates in a first direction, the cable 1520 winds onto the spindle, which raises the ferromagnetic element 1515 within the base 1505. As the spindle rotates in a second direction that is opposite the first direction, the cable 1520 unwinds from the spindle, which lowers the ferromagnetic element 1515 within the base 1505. The spindle can be powered by any type of actuator. In alternative embodiments, the element controller 1510 can include different components and/or operate in a different way to raise and lower the ferromagnetic element 1515. The cable 1520 which connects the element controller 1510 to the ferromagnetic element 1515 can be a wire, string, fiber, etc.

FIG. 15C is a side view of an induction heating system with a plurality of moving ferromagnetic elements and a plurality of EM radiation sources in accordance with an illustrative embodiment. As shown, the base 1505 of the system in FIG. 15C includes three EM radiation sources 1500 mounted thereto. A separate emission area 1525 is associated with each of the EM radiation sources 1500. While three EM radiation sources are shown, the system can include additional EM radiation sources in alternative embodiments, such as 4, 5, 8, 10, etc. As shown, a first ferromagnetic element 1515 is positioned in an emission area 1525 that is lowest in the base 1500, and a second ferromagnetic element 1515 is positioned in an emission area 1525 that is at a center of the base 1505. In the view of FIG. 15C, there is no ferromagnetic element in the uppermost emission area 1525.

The EM radiation sources 1500 can emit radiation having the same intensities, or alternatively each of the EM radiation sources 1500 may emit radiation at a different intensity to control the amount of heating that results in the associated emission areas. For example, the lowermost EM radiation source 1500 can emit a first radiation having a highest intensity, the central EM radiation source 1500 can emit a second radiation having a medium intensity, and the uppermost EM radiation source 1500 can emit a third radiation having a lowest intensity. The amount of heating can therefore be controlled by controlling which emission area the ferromagnetic elements 1515 are positioned in. In an illustrative embodiment, the intensities of the EM radiation sources 1500 can all be adjustable depending on the application. Thus, in some applications, the lowest emission area may have the lowest intensity and the uppermost emission area may have a higher (or the highest) intensity of radiation.

In some embodiments, the base 1505 can include a plurality of the temperature sensors 1530 positioned about the base 1505. The plurality of temperature sensors 1530 can be used to monitor the temperatures in a plurality of different areas of the base 1505, and the ferromagnetic elements can be moved into various emission areas 1525 based on the monitoring. For example, a user may specify that a desired temperature for the contents of the base 1505 is 180 degrees Fahrenheit. A temperature sensor toward a top of the base 1505 can indicate that the detected temperature is 170 degrees. As a result, one or more ferromagnetic elements can be moved to the uppermost emission area to provide further heat to the top of the base 1505. Similarly, a temperature sensor toward the bottom of the base 1505 can indicate that the detected temperature is 186 degrees. In response, any ferromagnetic elements present in the lowermost emission area can be removed therefrom to reduce the heat of that portion of the base 1505 (and its contents).

FIG. 15D is a side view of an induction heating system with a plurality of moving ferromagnetic elements and a plurality of EM radiation sources in accordance with another illustrative embodiment. As shown in FIG. 15D, the EM radiation sources 1500 are positioned at a bottom of the base 1505. Alternatively, the EM radiation sources 1500 could be positioned at a top of the base 1505 and/or on a lid that fits onto the top of the base 1505. The positions of the EM radiation sources result in vertical emission areas 1525, as shown. In alternative embodiments, the emission areas can be at a diagonal angle relative to a bottom of the base 1505. The ferromagnetic elements 1515 move horizontally between a pair of element controllers 1510. In some embodiments, each ferromagnetic element 1515 can be associated with a single element controller, and the cable 1520 that supports the ferromagnetic elements can be mounted opposite the single element controller. The configuration of FIG. 15D allows the ferromagnetic elements 1515 to move horizontally into and out of the various emission areas to control the overall temperature of the base 1505 and its contents based on sensed values from temperature sensor(s) 1530 mounted to the base. As shown, the base 1505 includes a plurality of temperatures sensors mounted thereto that are used to monitor temperature.

Figure 16:
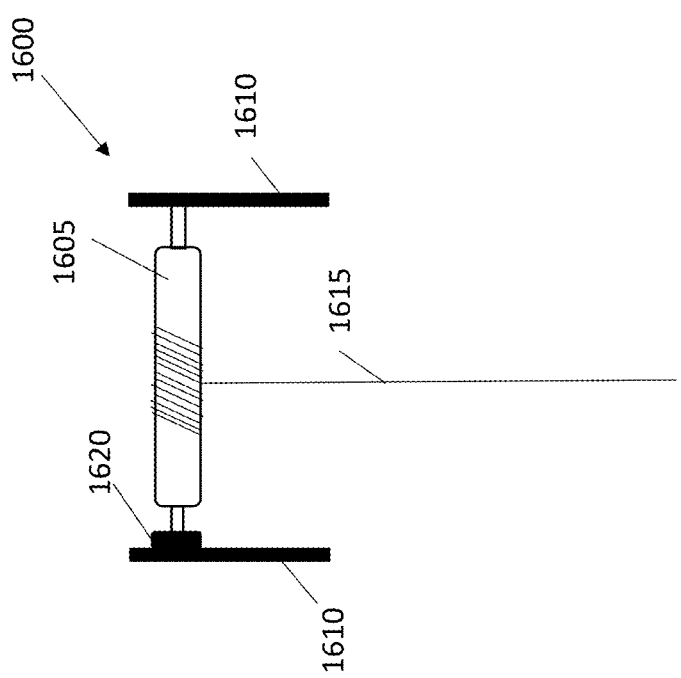
FIG. 16 is a sectional view of an element controller in accordance with an illustrative embodiment.

FIG. 16 is a sectional view of an element controller 1600 in accordance with an illustrative embodiment. The element controller 1600 (which can be, e.g., the element controller 1510 depicted in FIG. 15) includes a spindle 1605 that is rotatably mounted to sidewalls 1610 of the controller. A cable 1615 is wound around the spindle 1605. As the spindle 1605 rotates in a first direction, the cable 1615 is released from the spindle 1605 such that a ferromagnetic element (not shown) mounted to the end of the cable 1615 is lowered (in the orientation depicted in FIG. 16). As the spindle 1605 rotates in a second direction that is opposite the first direction, the cable 1615 is wound onto the spindle 1605 such that a ferromagnetic element mounted to the end of the cable 1615 is raised (in the orientation depicted in FIG. 16). The rotation is controlled by an actuator 1620 that bi-directionally rotates the spindle 1605. Any type of actuator can be used.

The actuator 1620 can be controlled by a computing system that is incorporated into the element controller 1600 or in wired/wireless communication with the element controller 1600. The computing system can include any of the computing components described herein such as a processor, memory, transceiver, interface, etc. In an illustrative embodiment, the memory of the computing system stores a heating algorithm that controls the positioning of the ferromagnetic elements to achieve and maintain a desired temperature. For example, the interface of the computing system can receive a desired temperature or desired temperature range from a user. The processor receives temperature data from the temperature sensor(s) positioned about the base of the system and/or temperature sensors positioned in/on the ferromagnetic elements. The processor can then move the ferromagnetic elements to achieve and maintain the desired temperature at each location of the base. For example, all of the ferromagnetic elements can be positioned in an emission zone such that they are heated. The elements can be positioned in the same emission zone or in different emission zones to more evenly heat the contents of the base. Once the temperature is reached, one or more of the ferromagnetic elements are removed from an emission zone and/or moved into an emission zone having a lower intensity (which results in less heat being generated). The processor can also control the intensity in each emission zone to help control the temperature.

Figure 17:
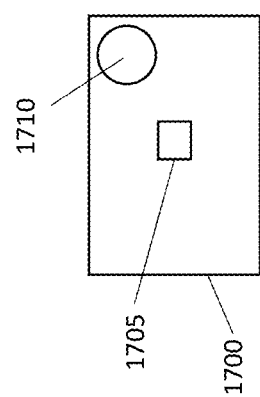
FIG. 17 depicts a ferromagnetic element in accordance with an illustrative embodiment.

FIG. 17 depicts a ferromagnetic element 1700 in accordance with an illustrative embodiment. The ferromagnetic element 1700 includes a temperature sensor 1705 mounted thereto. The temperature sensor 1705 can be mounted to an external surface of the ferromagnetic element 1700 or embedded within the ferromagnetic element 1700 depending on the embodiment. The temperature sensor 1705 is used to determine the temperature of the element 1700 and/or its surroundings. The ferromagnetic element 1700 also includes a port 1710, which allows the ferromagnetic element 1700 to adjust its buoyancy so that it raises/lowers within a liquid. For example, the port 1710 can open receive liquid such that the ferromagnetic element 1700 loses buoyancy and sinks within the liquid until it is within an emission zone. The port 1710 can similarly expel the liquid so that the ferromagnetic element 1700 floats upward in the liquid and exits the emission zone. The port 1710 receives/expels the liquid based on readings from the temperature sensor 1705. A bi-directional pump can be included in the ferromagnetic element 1700 in some embodiments to control the receiving/expelling of liquid. Thus, the port 1710 allows the ferromagnetic element 1700 to position itself within an emission zone to be heated, and to position itself outside of the emission zone so that it is no longer heated, depending on the desired temperature set by the user. The liquid in which the ferromagnetic element 1700 is positioned can be in the cavity between double walls of the base, or in an interior of the base, depending on the embodiment.

In the implementation of FIG. 17, the ferromagnetic element can move without the use of a separate element controller and cable. Rather, the movement occurs via adjustment of the buoyancy of the ferromagnetic element 1700 within a liquid. In an alternative embodiment (e.g., the embodiment of FIG. 15), the port 1710 may not be included and an element controller can be used. In such an embodiment, the temperature sensor 1705 can still be mounted to the ferromagnetic element 1700 and used by an element controller to determine the appropriate position for the element. In another alternative embodiment, the ferromagnetic element 1700 may not include a temperature sensor.

It should be understood that the disclosed embodiments have been described to provide the best illustration of the principles of the subject matter and its practical application to thereby enable one of ordinary skill in the art to utilize the system in various embodiments and with various modifications as are suited to the particular use contemplated.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A method for performing mold remediation, the method comprising:
    placing a ferromagnetic material in or adjacent to a surface upon which mold is located;
    emitting, by an electromagnetic radiation source, radiation to heat the ferromagnetic material that is adjacent to the surface upon which the mold is located; and
    detecting, by a temperature sensor, a temperature of the surface to monitor mold remediation.

2. The method of claim 1, wherein the surface comprises a wall or ceiling, and wherein placing the ferromagnetic material comprises:
    forming an opening in the wall or ceiling; and
    injecting the ferromagnetic material into the opening formed in the wall or ceiling.

3. The method of claim 2, wherein forming the opening in the wall or ceiling comprises drilling into the wall or ceiling to form the opening.

4. The method of claim 2, wherein the ferromagnetic material comprises a plurality of ferromagnetic particles incorporated into a spray insulation.

5. The method of claim 4, wherein the spray insulation is expandable such that at least a portion of the spray insulation and at least a portion of the plurality of ferromagnetic particles come into contact with the mold.

6. The method of claim 4, wherein injecting the ferromagnetic material comprises spraying the spray insulation through the opening formed in the wall or ceiling.

7. The method of claim 1, wherein the ferromagnetic material comprises a plurality of ferromagnetic particles incorporated into fiberglass insulation.

8. The method of claim 1, further comprising comparing, by a processor in communication with the electromagnetic radiation source and the temperature sensor, the temperature of the surface to a desired temperature to perform mold remediation.

9. The method of claim 8, further comprising controlling, by the processor, an amount of the electromagnetic radiation emitted by the electromagnetic radiation source based at least in part on the desired temperature.

10. The method of claim 8, further comprising controlling, by the processor, an amount of the electromagnetic radiation based at least in part on an ambient temperature of the surface.

11. The method of claim 1, further comprising using a timer to monitor a time duration for which the desired temperature is maintained.

12. The method of claim 11, further comprising comparing, by a processor in communication with the electromagnetic radiation source and the temperature sensor, the time duration to a desired time duration to determine whether mold remediation is complete.

13. The method of claim 12, further comprising turning off the electromagnetic radiation source, by the processor, responsive to a determination that the mold remediation is complete.

14. The method of claim 1, wherein placing the ferromagnetic material comprises embedding a plurality of ferromagnetic particles into the surface.

15. The method of claim 1, wherein placing the ferromagnetic material comprises adhering a ferromagnetic sheet to the surface.

16. The method of claim 1, wherein placing the ferromagnetic material comprises adhering a ferromagnetic mesh to the surface.

17. The method of claim 1, further comprising mounting a housing to the surface, wherein the housing is configured to house at least the processor and the electromagnetic radiation source.

18. The method of claim 1, wherein the temperature sensor comprises a plurality of temperature sensors.

19. The method of claim 18, further comprising positioning the plurality of temperature sensors in an array about the surface.

20. The method of claim 18, further comprising monitoring, by a processor in communication with the electromagnetic radiation source and the temperature sensor, the plurality of temperature sensors, wherein the detected temperature of the surface comprises a lowest temperature detected from the plurality of temperature sensors.

* * * * *